(12) United States Patent
Nguyen

(10) Patent No.: US 6,835,190 B2
(45) Date of Patent: Dec. 28, 2004

(54) RETRACTABLE SAFETY INFUSION NEEDLE

(75) Inventor: Steven Huu Nguyen, Somerset, NJ (US)

(73) Assignee: Smiths Medical ASD, Inc., Keene, NH (US)

( * ) Notice: Subject to any disclaimer, the term of this patent is extended or adjusted under 35 U.S.C. 154(b) by 0 days.

(21) Appl. No.: 10/123,516

(22) Filed: Apr. 17, 2002

(65) Prior Publication Data

US 2003/0199830 A1 Oct. 23, 2003

(51) Int. Cl.⁷ .......................... A61M 5/00; A61M 5/32; A61B 5/00
(52) U.S. Cl. ...................... 604/198; 604/171; 604/110; 604/197; 604/263; 600/573
(58) Field of Search .................. 604/110–198, 263; 600/573, 576

(56) References Cited

U.S. PATENT DOCUMENTS

| | | |
|---|---|---|
| 4,192,304 A | 3/1980 | Millet |
| 4,326,519 A | 4/1982 | D'Alo et al. |
| 4,676,783 A | 6/1987 | Jagger et al. |
| 4,781,692 A | 11/1988 | Jagger et al. |
| 5,067,946 A | 11/1991 | Zhadanov |
| 5,112,311 A | 5/1992 | Utterberg et al. |
| 5,195,985 A | 3/1993 | Hall |
| 5,312,361 A | 5/1994 | Zadini et al. |
| 5,330,438 A | 7/1994 | Gollobin et al. |
| 5,382,240 A | 1/1995 | Lam |
| 5,480,388 A | 1/1996 | Zadini et al. |
| 5,498,241 A | 3/1996 | Fabozzi |
| 5,549,571 A | 8/1996 | Sak |
| 5,562,636 A | 10/1996 | Utterberg |
| 5,562,637 A | 10/1996 | Utterberg |
| 5,573,512 A | 11/1996 | van den Haak |
| 5,575,777 A * | 11/1996 | Cover et al. ................. 604/198 |
| 5,704,917 A | 1/1998 | Utterberg |
| 5,746,215 A * | 5/1998 | Manjarrez ................... 600/573 |
| 5,779,679 A | 7/1998 | Shaw |
| 5,800,400 A | 9/1998 | Hogan |
| 5,858,004 A | 1/1999 | Shields |
| 5,921,969 A | 7/1999 | Vallelunga et al. |
| 5,928,199 A | 7/1999 | Nakagami |
| 5,931,815 A | 8/1999 | Liu |
| 5,951,529 A | 9/1999 | Utterberg |
| 5,968,016 A | 10/1999 | Yerfino et al. |
| 6,090,078 A * | 7/2000 | Erskine ....................... 604/198 |
| RE36,885 E | 9/2000 | Blecher et al. |
| 6,210,371 B1 * | 4/2001 | Shaw ..................... 604/164.08 |
| 6,228,066 B1 | 5/2001 | Zhadanov et al. |
| RE37,439 E | 11/2001 | Firth et al. |
| 2001/0053886 A1 | 12/2001 | Caizza |
| 2002/0007147 A1 | 1/2002 | Capes et al. |

* cited by examiner

Primary Examiner—Nicholas D. Lucchesi
Assistant Examiner—Roz Maiorino
(74) Attorney, Agent, or Firm—Louis Woo

(57) ABSTRACT

A needle device, possibly in the form of a butterfly or IV needle, has a housing with an orthogonal passage to the bore of the housing. A key that has a non-uniform opening with spaces defined by the opposing inner walls of its two extending legs is inserted into the passage. By positioning the key at different placement locations relative to the passage so that the different dimensioned spaces of the opening become aligned with the bore of the housing, the needle assembly can be selectively retained at at least a first position whereby the needle is extended out of the housing, and a second position whereby the needle is permanently retracted within the housing after use.

22 Claims, 32 Drawing Sheets

RETRACTABLE SAFETY INFUSION NEEDLE

FIELD OF THE INVENTION

The present invention relates to a safety infusion needle assembly and more particularly to an infusion needle assembly whose needle is automatically retractable into the housing of the needle assembly after use for preventing the contaminated needle from further exposure.

BACKGROUND OF THE INVENTION

There are a number of retractable butterfly needle assemblies. U.S. Pat. No. 5,514,971 discloses a butterfly needle assembly whose needle is manually retracted into the housing. A retaining pin that biases against the body of the needle springs down when the needle clears it to prevent the retracted needle from further usage.

U.S. Pat. No. 5,746,215 discloses an IV needle assembly that has a needle that is automatically retractable. For the device of the '215 patent, a complicated system that includes rear and forward locking tabs at the needle hub coact with locking ribs at the needle housing for maintaining the needle at its extended or retracted position. To retract the needle into the housing using a tensioned spring, an extended bridge with two opposite portions has to be compressed by the user and be flattened.

U.S. Pat. No. 5,779,679 discloses a winged IV needle assembly that includes a pair of additional wings fitted with appropriate tabs for coacting against contact lugs at the needle hub for retracting the needle hub and its attached needle into the housing.

U.S. Pat. No. 5,968,016 discloses a winged needle device that requires the user to pull the wings in opposite direction to each other in order to deform the latches that hold the catch of the needle in place, so that the needle is retracted into the housing by a tensioned elastic tube.

U.S. Pat. No. 6,210,371 discloses a device that is similar to the '679 device in that an additional pair of wings, with the appropriate contact and tabs, is used for releasing the catch portion of the needle from catches at the housing to retract the needle into the housing.

The present invention winged needle device aims to improve upon the above-noted prior art devices, both in terms of simplicity in construction and use.

SUMMARY OF THE PRESENT INVENTION

To protect against accidental pricking, the contaminated needle of an IV or butterfly needle device is designed with an automatic retracting mechanism that is activated when the user pushes a button, or key, in a given direction. Once the mechanism is pushed or actuated, the needle is automatically retracted into the housing, and remains confined within the housing.

To achieve this end, the housing of the needle device of the instant invention is formed with a passage that communicates with the bore of the housing. The passage may be in the form of an upraised well, at either the front end or the rear portion of the housing. Alternatively, the passage may be in the form of a sleeve orthogonal to the housing. For the well passage embodiment, a push mechanism in the form of a push button is fitted into the well. The button is in the form of a base that has extending therefrom two legs into the well. The inside opposing portions of the two legs converge at their distal ends so that the opening formed by the two legs is non-uniform, as the space or aperture defined by the inner opposing walls of the two legs that are not converged towards each other has a dimension that is greater than the space defined by the converging inner portions of the two legs. The well is formed on the housing such that, when the push mechanism is inserted thereinto, the different dimensioned spaces or apertures formed by the two legs would selectively intersect the bore of the housing, as the button and more specifically the space defined by the two legs of the button is in a transverse, or orthogonal, relationship to the longitudinal axis of the housing.

On the outside wall of each of the legs of the push button there are formed at least two one-way notches that coact with a corresponding catch extending from the inside wall of the well. The notches are formed at appropriate locations along the legs so that different placement locations are defined for the push button, relative to the housing. For the exemplar embodiments, such placement locations represent a first position whereat the space defined by the converged inner portions of the two legs intersects the bore of the housing. The second placement location is defined when the push button is further positioned toward the housing so that the space defined by the inner non-converging portions of the two legs intersects the bore of the housing.

A needle assembly that has a needle hub and a needle extending therefrom is slidably fitted within the bore of the housing. The needle hub has a collar or a rib at a portion thereof that coacts with or abuts against a bias element in the housing such as for example a tensioned spring or elastic tube. While the one side of the collar is being biased by the tensioned bias element, the other side of the collar is abutted by the converged legs of the push button so that the needle extending from the needle hub continues to extend out of the housing for use with a patient at the first placement location of the push button.

After use, the push button is moved closer relative to the housing so that, in the case that it is fitted to a well upraised from the housing, the top of the push button becomes flush with the top rim of the well. At that point, the space defined by the non-converging portions of the legs extending from the button intersects the bore of the housing such that the collar about the needle hub would pass through the space due to the biasing force exerted by the bias element. Consequently, as the needle hub is biased toward the end of the housing, the needle that extends from the needle hub is retracted within the housing. A stopper at the end of the housing maintains the front portion of the needle hub within the housing, as the collar abuts the stopper. The contaminated needle is therefore retained within the housing.

To prevent the push button from being inadvertently pushed down, particularly when the needle is inserted into a patient, a safety lock, in the form of a safety button or plug, is fitted to a cavity of the push button. While the push button is at its first placement location, the space defined by the converged portions of its legs intersects the bore of the housing. The safety lock is ordinarily biased away from the cavity of the push button so that it prevents the push button from being pushed into the well. It is only after the needle has been withdrawn from the patient and the safety lock pushed into the cavity of the push button that the push button may be pushed into the well to its second placement location where the space defined by the non-converging portions of its legs intersects the bore of the housing. Coacting mechanisms in the form of notches at the legs and catches at the inner wall of the well maintain the push button at the respective first and second placement locations.

A second embodiment of the instant invention needle device utilizes a push button that, in addition to being able to be selectively positioned at first and second placement locations, also has flaps that prevent the needle hub from completely passing out of the housing, once the push button is pressed to its placement location that allows retraction of the needle into the housing. For this embodiment, the push button may be located at the end portion of the housing.

Yet another embodiment of the instant invention needle device integrates a sleeve at the distal portion of the housing. A key is inserted to the sleeve and is movable to at least a first and second placement location orthogonal to the longitudinal axis of the housing. The key is formed with a non-uniform opening, with differently dimensioned apertures, one of which would prevent the movement of the needle hub, while the other would allow the needle hub to pass through for retracting the needle into the housing. Coacting teeth at the sleeve and key maintain the placement of the key until the user manually pushes the key. Further, the teeth at the key are one-way teeth, so that once pushed to the placement location enabling the retraction of the needle, the key could no longer be repositioned to its first placement location.

BRIEF DESCRIPTION OF THE FIGURES

The present invention will become apparent and the invention will be best understood with reference to the following description of embodiments of the present invention taken in conjunction with the accompanying drawings, wherein.

DETAILED DESCRIPTION OF THE EMBODIMENTS OF THE INVENTION

Figure 1:
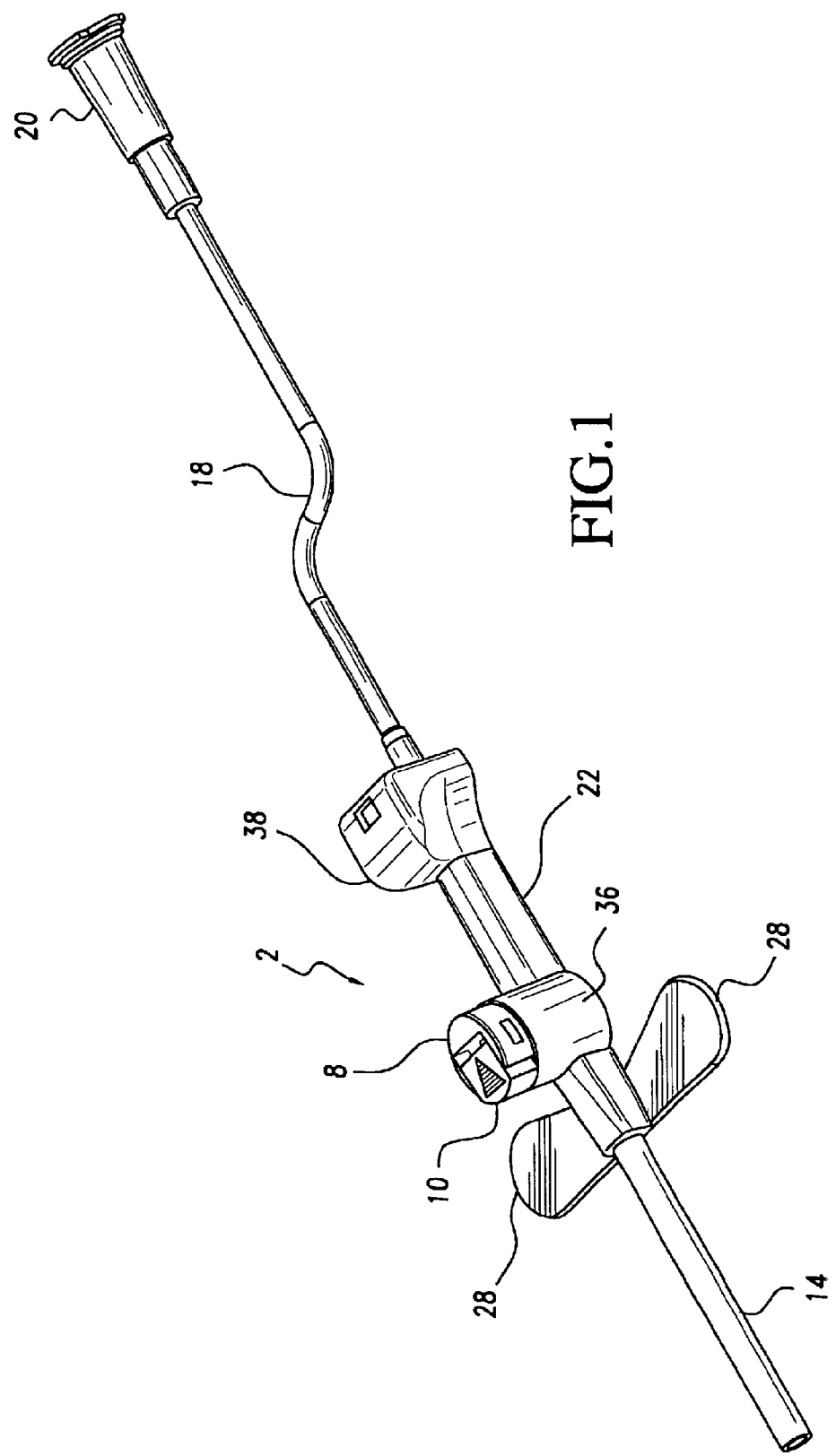
FIG. 1 is a perspective view of a first embodiment of the instant invention needle device.
Figure 2:
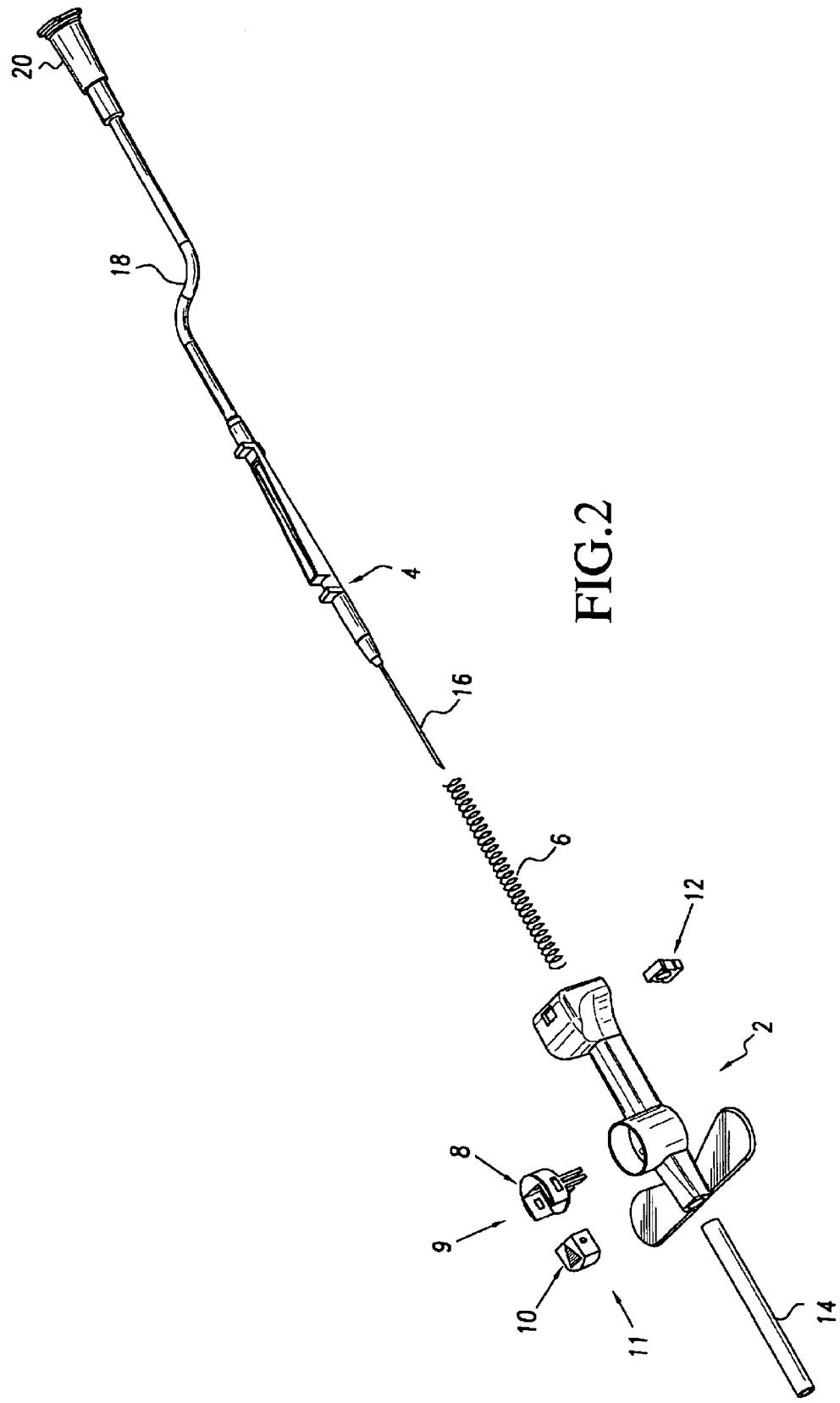
FIG. 2 is a disassembled view of the needle device of FIG. 1.

With reference to FIGS. 1–13, a first embodiment of the needle device of the instant invention is described. Specifically, the IV or butterfly needle device of the instant invention is shown to have a housing 2, a needle assembly 4, a bias element 6 in the form of a spring, a push mechanism 8, a safety lock element 10 and a stopper element 12. A sheath 14 is used to cover the needle 16 before the device is used. An infusion tube (or medicament line) 18 is mated to the aft portion of the needle assembly 4. A luer connector 20 at the end of the infusion line 18 provides coupling to either a fluid source or a fluid storage.

Figure 3:
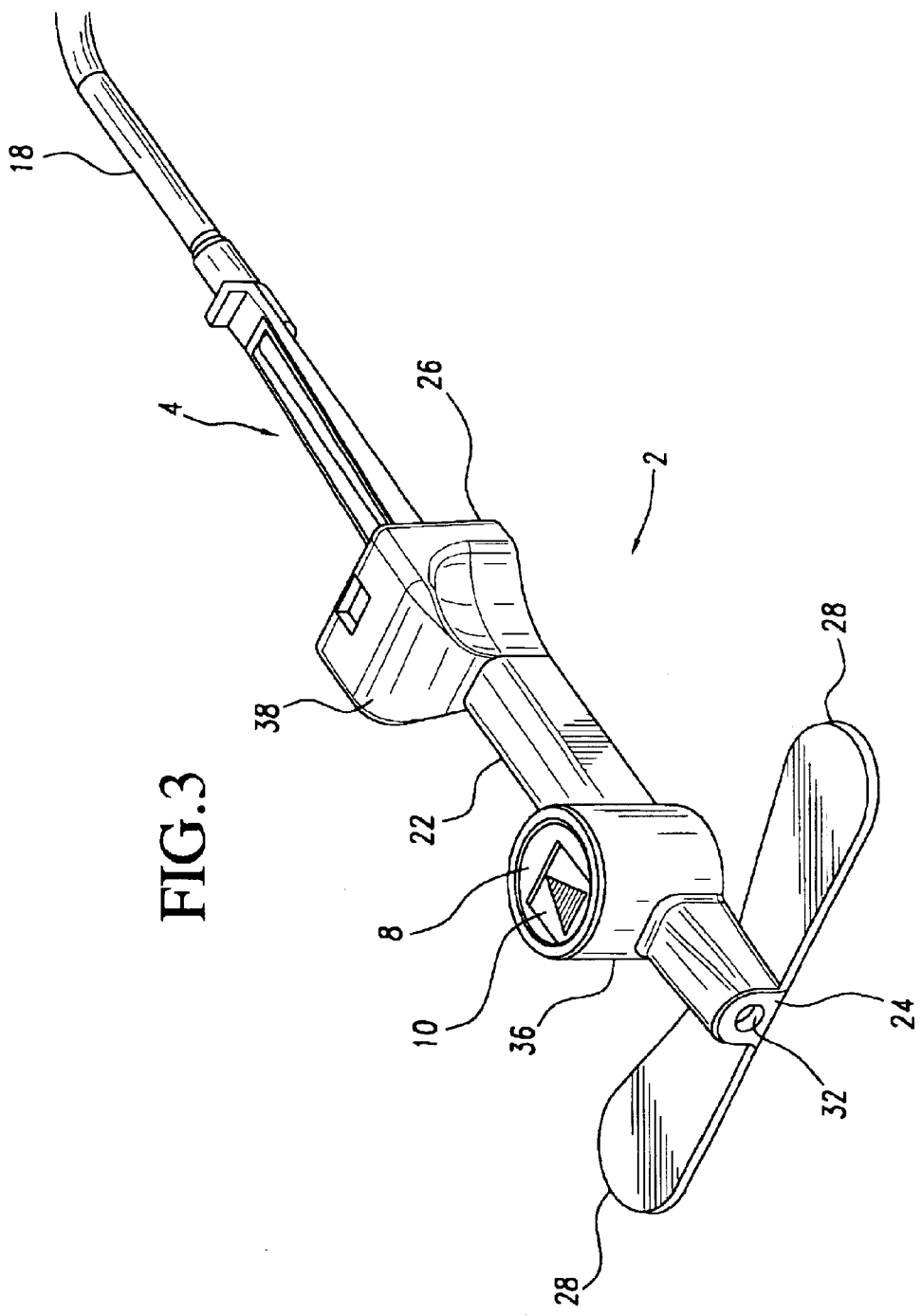
FIG. 3 is a perspective view of the FIG. 1 device with the needle having been retracted into the housing.
Figure 4:
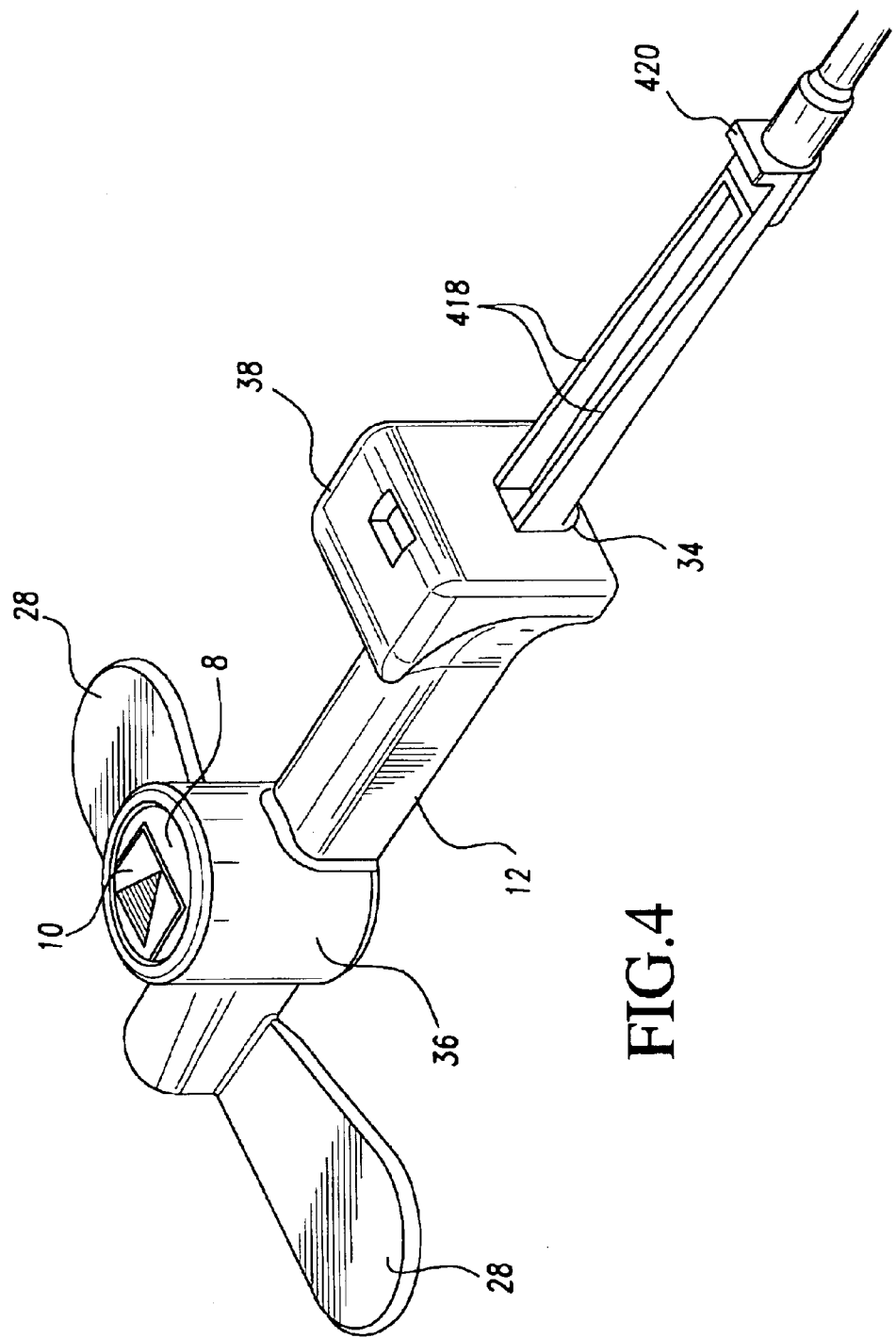
FIG. 4 is a back view of the FIG. 3 device.
Figure 9:
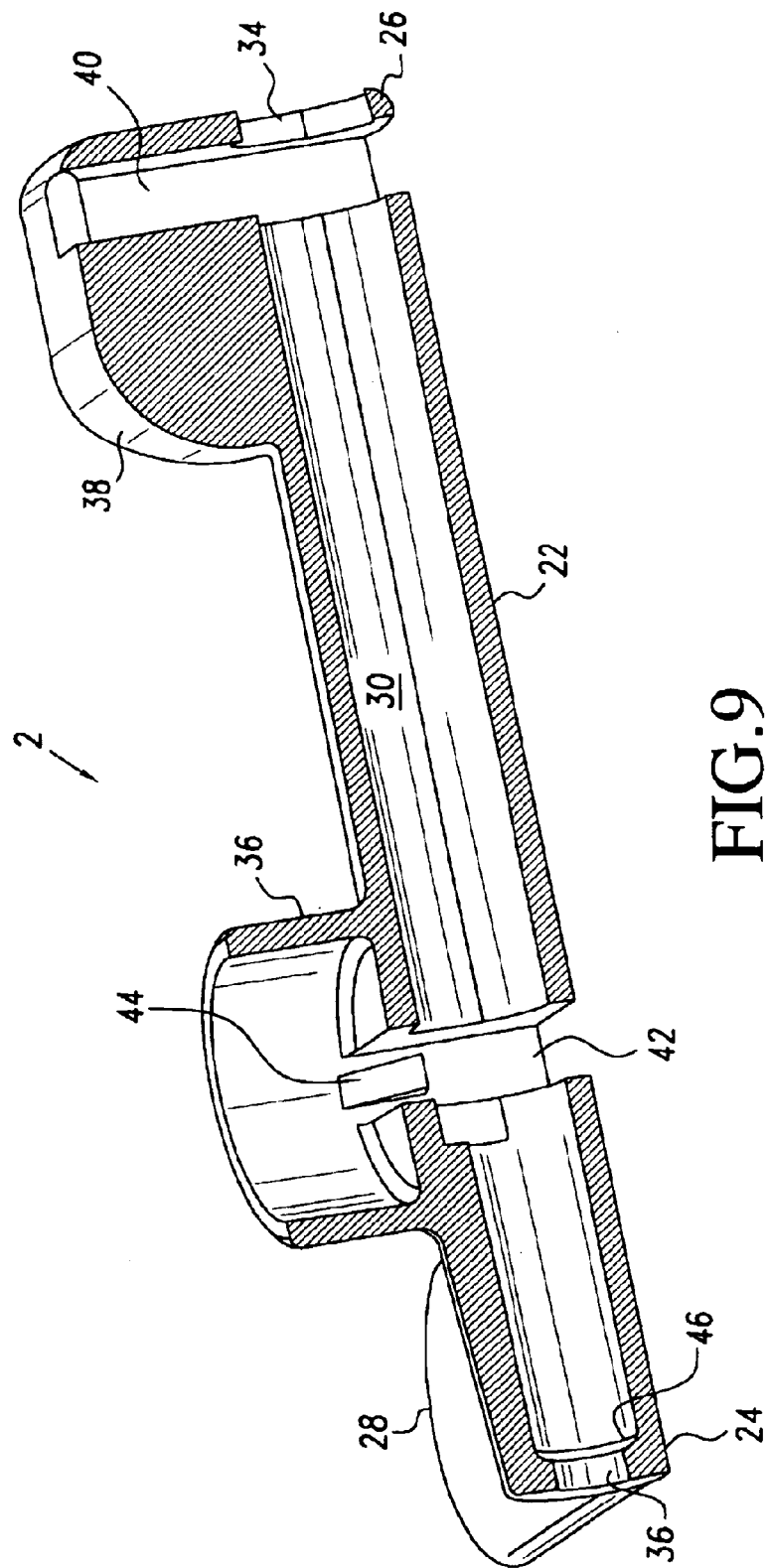
FIG. 9 is a cut-away exposed view of the housing of the FIG. 1 device.

As best shown in FIGS. 1, 3 and 9, housing 2 includes a longitudinal housing proper 22 that has a first (front or distal) end 24 and a second (rear or proximal) end 26. Foldably extending from the front end 24 of housing 22 are two wings 28. A bore 30 extends throughout the length of housing 22, with a first opening 32 provided at front end 24 and a second opening 34 provided at rear end 26 of housing 22. Thus, a clear path extends from front opening 32 through bore 30 to rear opening 34.

Integrally rising from housing 22 at the front or mid section thereof is a well structure 36. Housing 22 has also a raised portion 38 integrated to its proximal end. As shown, a void 40 is provided within upraised portion 38 orthogonal to the longitudinal axis of housing 22 for intersecting bore 30. Well 36 likewise has a passage 42 that communicates with bore 30. As shown, passage 42 is orthogonal to the longitudinal axis of housing 22 and intersects bore 30. Further shown within well 36, at approximately the mid section thereof, is a catch 44. The purpose of catch 44 will be discussed later.

Figure 8:
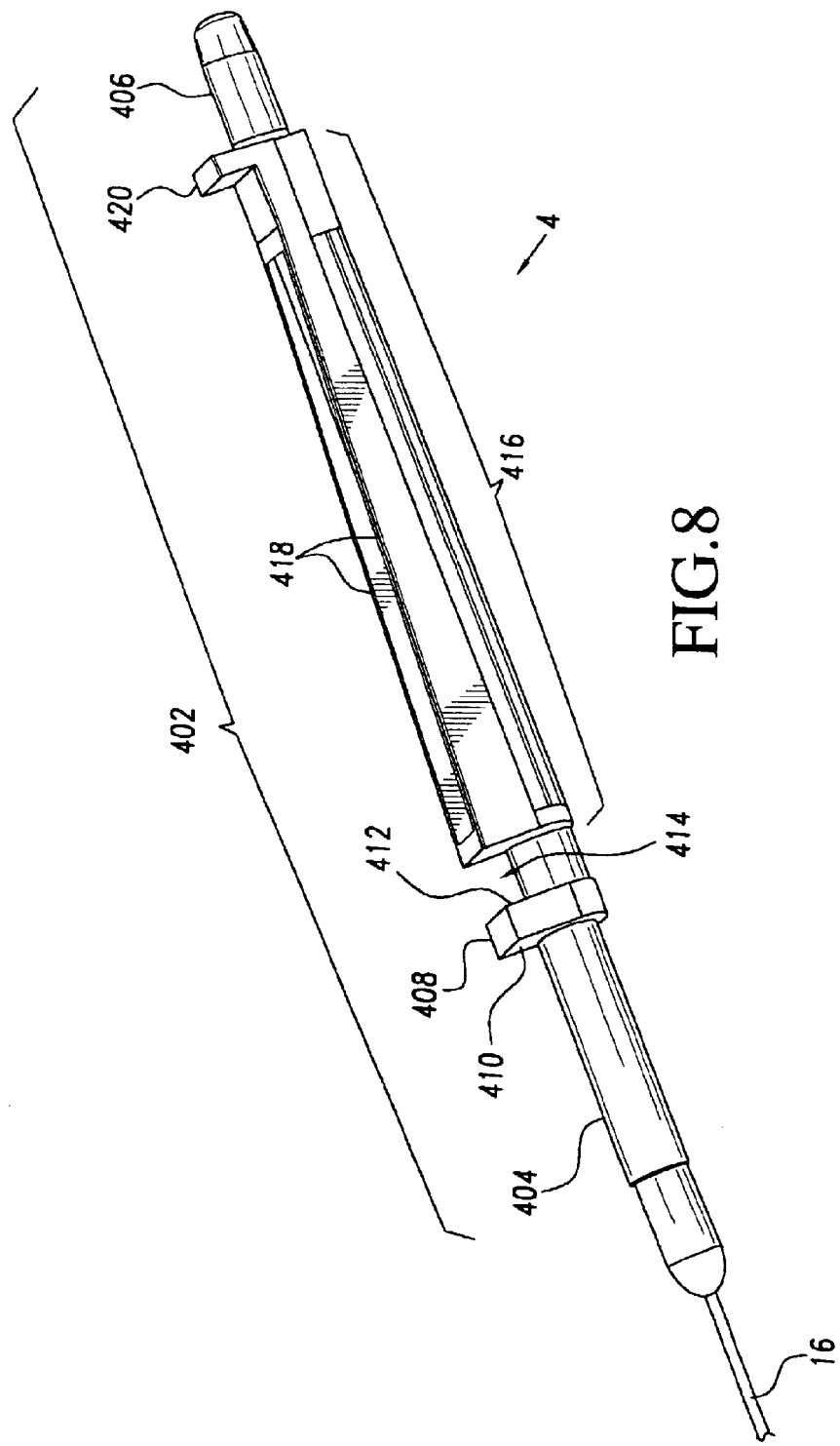
FIG. 8 shows the needle assembly of the instant invention device of FIG. 1

Slidably fitted within bore 30 of housing 22 is needle assembly 4. As best shown in FIG. 8, needle assembly 4 has a needle hub 402 having attached thereto needle 16. Needle hub 402 has a front end extension 404 to which needle 16 is attached and a rear end 406 to which infusion line 18 is coupled. A collar or rib 408 is formed at the end of extension 404. Collar 408 has a given dimension so that spring 6, when fitted into bore 30, is booked-ended by inner surface 46 at front end 24 of housing 22 and the front surface 410 of collar 408. Thus, once needle assembly 4 is slidably fitted within bore 30 of housing 22, spring 6 is compressed in tension.

Collar 408 has a rear surface 412, which becomes the front boundary of a groove 414 formed on the needle hub. The remaining portion 416 of the needle hub is configured to have a substantially rectangular guide configuration for the instant embodiment, with the top surface of the needle hub having respective top edges 418 that slants from the front to the rear, so as to form a declining surface. At the very end of surface 418 a wall or rib 420 is formed. The dimension of wall 420 may be substantially the same as opening 34, thereby allowing a substantial portion of needle hub 402 to pass out of housing 22.

Figure 5:
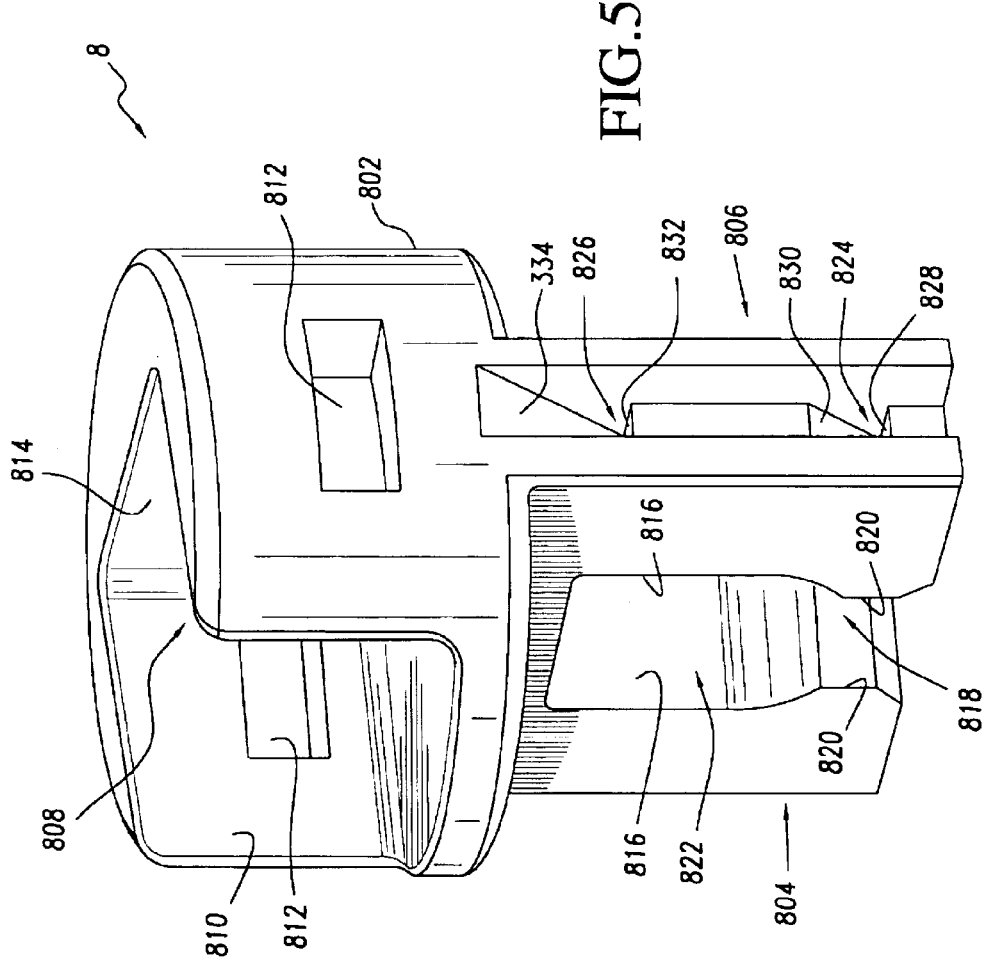
FIG. 5 is a perspective view of the push mechanism of the FIG. 1 device.
Figure 6:
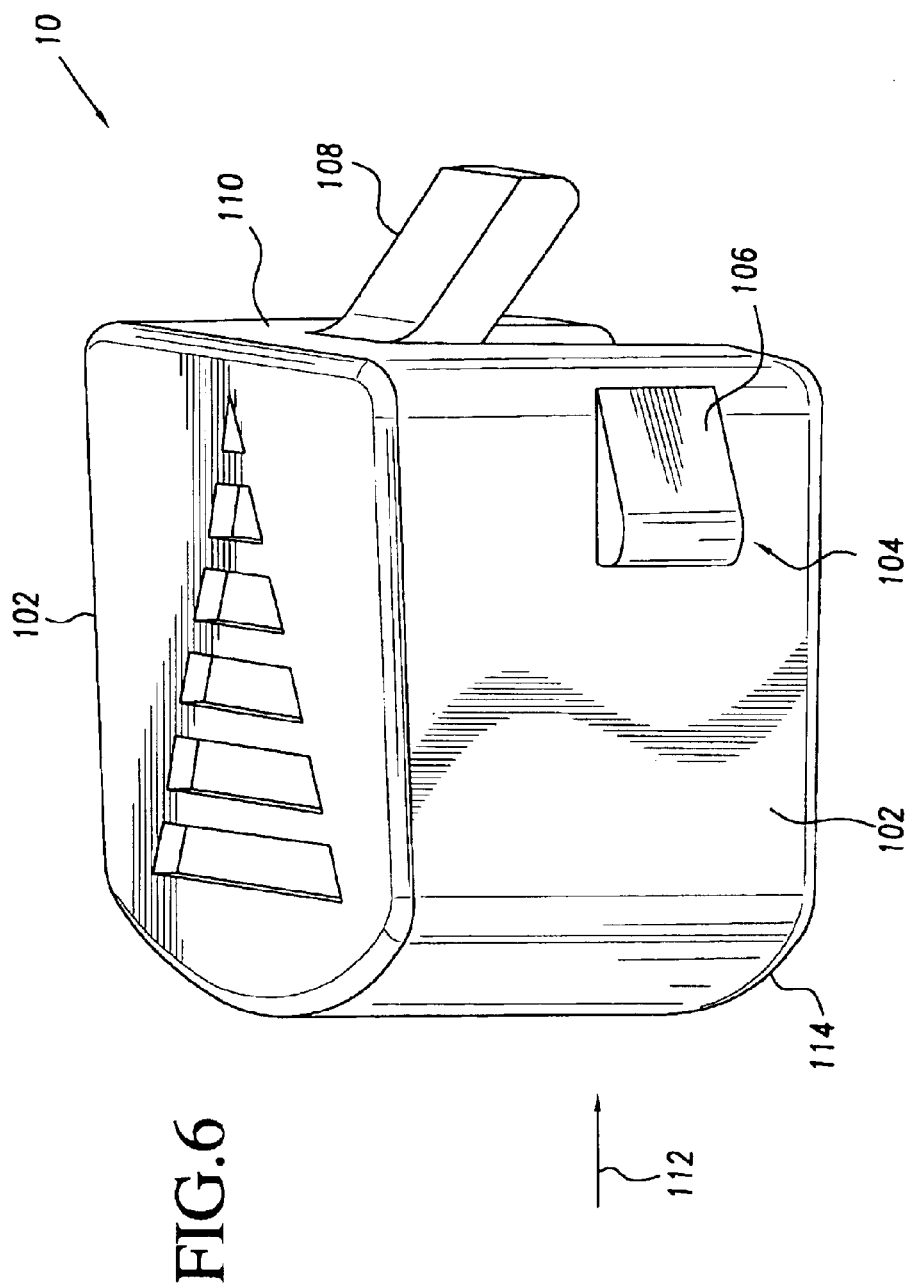
FIG. 6 is a perspective view of a safety lock for the FIG. 1 device.

With respect to FIG. 5, the push element or mechanism 8 of the first embodiment of the instant invention needle device is shown to comprise a push button or push button key having a base 802 with two legs 804 and 806 extending therefrom. Push button base 802 is shown to have a shape that enables it to slidably fit within well 36 of housing 22. A cavity or void 808 is formed at base 802. The dimension of cavity 808 is such that the safety lock stop 10 (FIG. 6) is fittable thereinto. As shown, safety stop 10 is in the shape of a plug that has two sidewalls 102 that slidably fit to the inner sidewalls 810 of push button 8. At each of the sidewalls 102 of safety stop 10 there is an extension 104 that has an incline surface 106 that fits within slot 812 of push key 802. A bias finger 108 extends from back wall 110 of safety stop 10 so that once plug 10 is fitted to cavity 808, unless a force is exerted against safety stop 10 along the direction as indicated by directional arrow 112, bias finger 108 will maintain safety stop 10 at the position as shown for example in FIG. 1, so that the front portion 114 of safety stop 10 acts against the top edge or rim of well 36 to prevent push button key 8 from being pushed into well 36. Once fitted to cavity 808, finger 108 biases against wall 814 of the base of push button key 8.

As was noted earlier, legs 804 and 806 extend from base 802 of push button key 8. As shown in FIG. 5, the inside walls, as designated by 816, of legs 804 and 806 converge toward each other at the respective distal portions of the legs. Thus, the space 818 defined between opposing inner walls 820 is smaller than the space 822 defined by opposing inner walls 816. In fact, space 818 is formed to have a dimension that allows the distal ends of legs 804 and 806 to mate with groove 414 of needle hub 402, and yet at the same time coacts against the back surface 412 of collar 408 so as to prevent the movement of needle assembly 4 within bore 30 of housing 22. Space 822, on the other hand, is formed to have a dimension that is greater than the dimension of collar 408, so that collar 408 would pass between legs 804 and 806 by way of space 822, if collar 408 were to be aligned with space 822.

On the outside wall of each of legs 804 and 806, although only shown with respect to leg 806, there is a longitudinal opening that includes at least two notches 824 and 826. Notch 824 is formed by a flat base 828 intersecting an incline 830. Notch 826 is formed by a flat base 832 intersecting an incline 834. Although not shown, corresponding notches are formed on the outer wall of leg 804.

Figure 10:
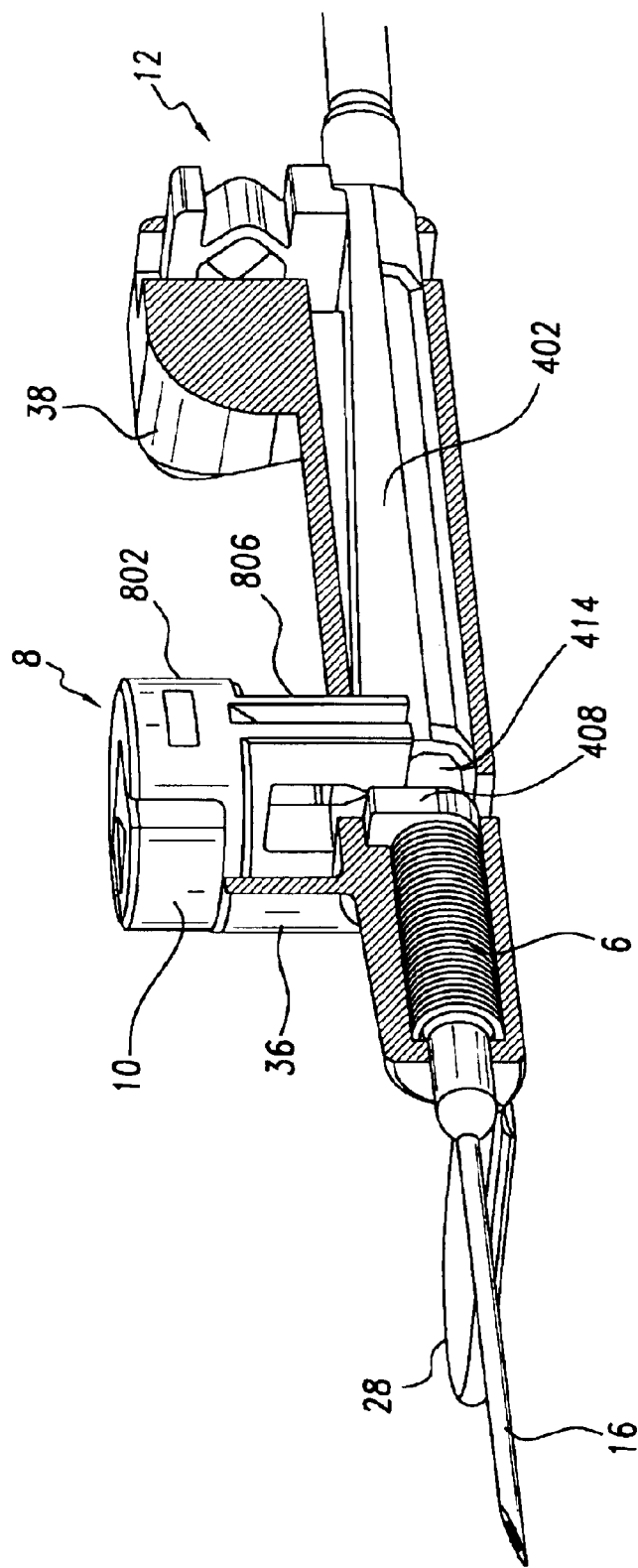
FIG. 10 is a cut-away view of the device of FIG. 1 showing the needle being extended out for usage.
Figure 11:
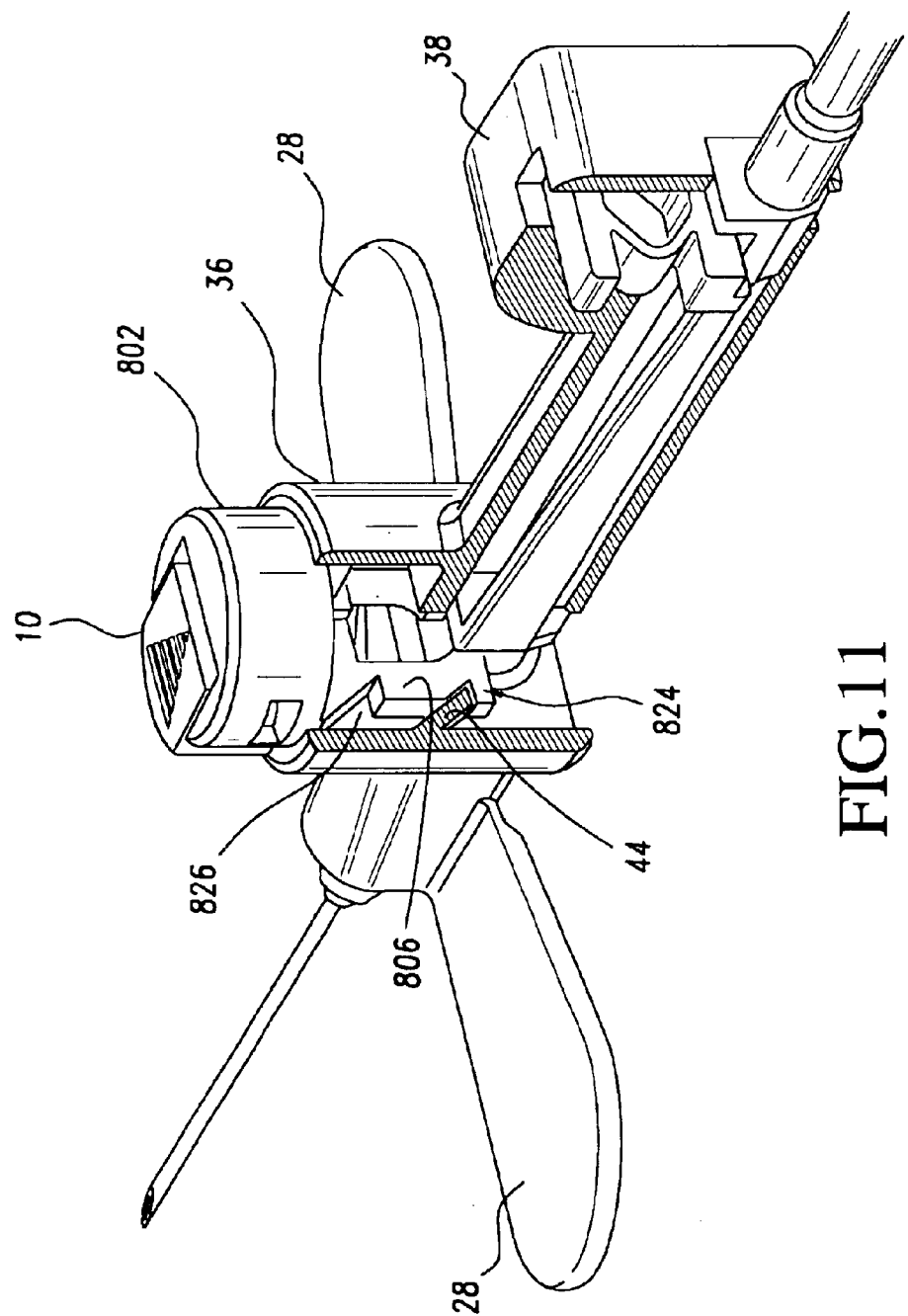
FIG. 11 is a back view of the FIG. 1 device showing the interaction between the push mechanism and the needle hub of the device.

With reference to FIGS. 9–11, push button key is shown to be inserted to well 36, with legs 804 and 806 straddling the portion of needle hub formed by groove 414. As best shown in FIG. 11, notch 824 of leg 806 of the push button key is shown to be engaged to catch 44 extending from the inner wall of well 36. A corresponding catch, not shown, extends from the opposing inner sidewall of well 36 and engages with the corresponding notch 824 formed on leg 804. As shown in this placement location, push button key 8, more specifically base 802 thereof, extends out of the mouth of well 36, with catch 44 engaged to notches 824. The converged inner walls 820 of the distal ends of legs 804 and 806 accordingly abut against the rear surface of 412 of rib or collar 408, thereby maintaining needle assembly 4 fixed relative to housing 2. As a consequence, needle 16 is fixedly extending out of opening 32 of housing 2, and can be used for insertion to a patient.

Figure 7:
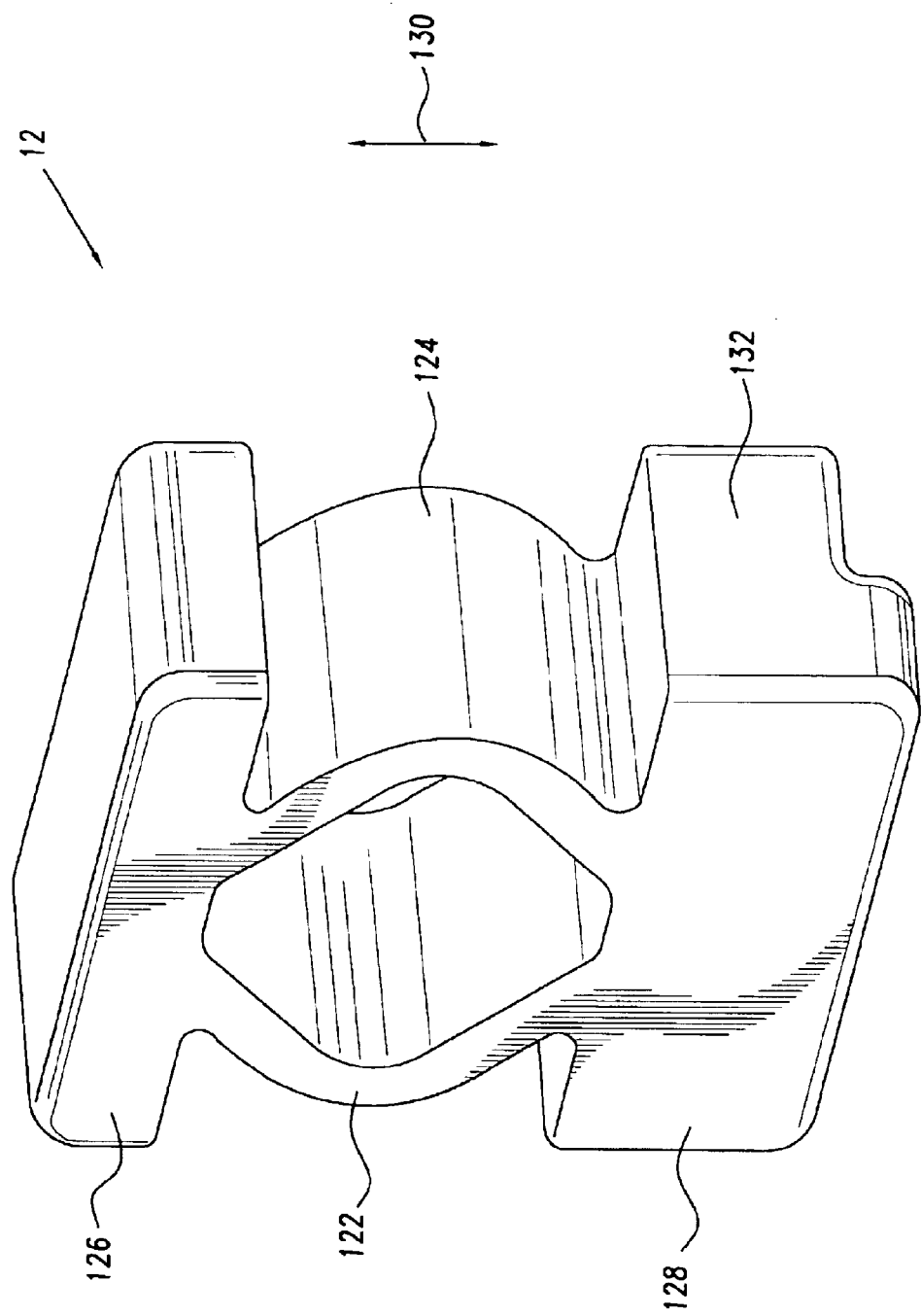
FIG. 7 is an exemplar stopper used in the FIG. 1 device.

FIG. 7 shows in greater detail the stopper element 12. Stopper 12 is a resilient member that is molded from an elastic material such as rubber so that its supports 122 and 124 that connect its top 126 to its base 128 act as springs to enable top 126 to move relative to base 128 along the directions as shown by bidirectional arrow 130. Stopper element 12 is dimensioned such that it fits in groove 40 of upraised member 38 at the back end of housing 22. Also, the side or cross section of stopper 12, designated 132, is molded to have a dimension that is slightly less than the width of groove 414. Thus, given its elasticity, the bottom of base 128 will continuously bias against the inclined edges 418 of needle hub 416 until groove 114 is aligned beneath it. At which time, base 128 will fall within groove 114 and abut against the back surface 412 of collar 408 to thereby stop any further movement of needle hub 402.

Figure 12:
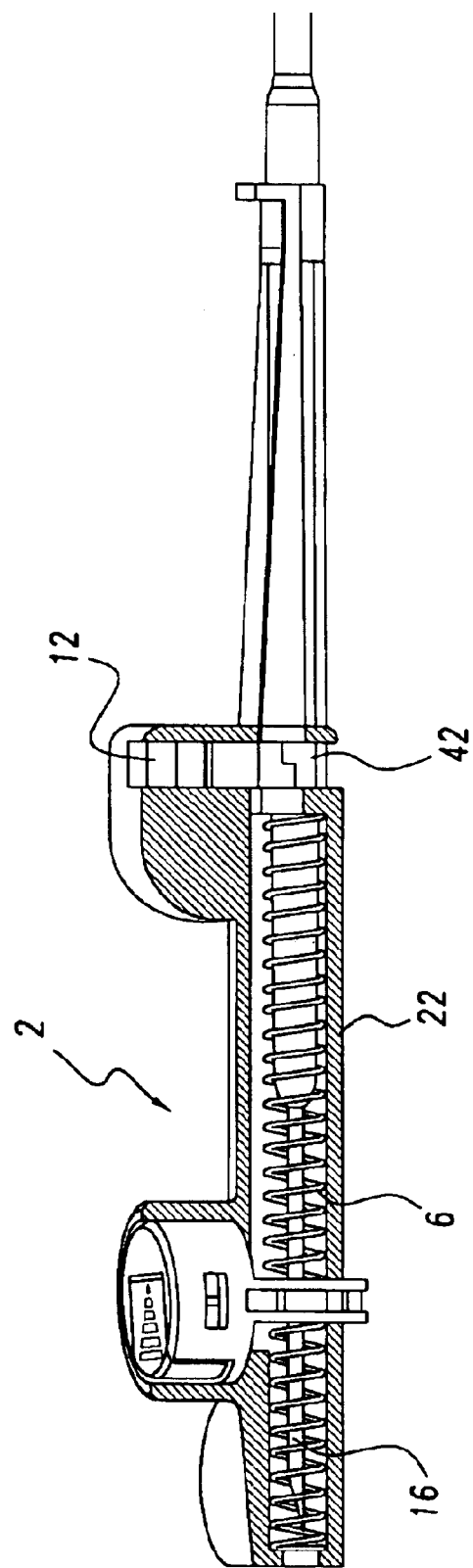
FIG. 12 is a cut-away side view of the device of FIG. 1 showing the needle having been retracted within the housing.
Figure 13:
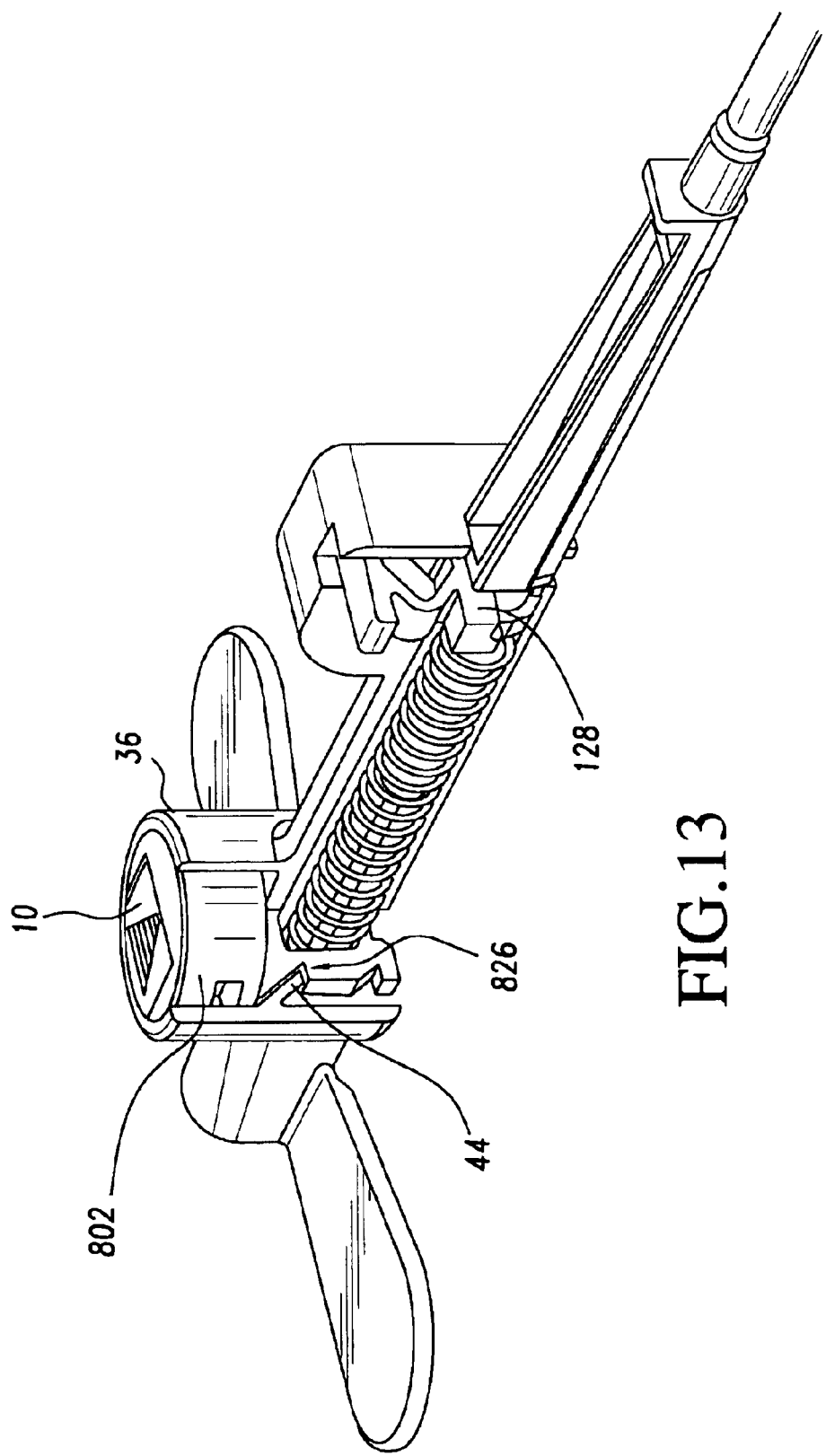
FIG. 13 is a semi cut-away back view of the needle device of FIG. 1 showing the needle having been retracted within the housing of the device.

FIGS. 12 and 13 show that needle 16 has been retracted within housing 2, so that the tip of the needle is no longer exposed to the environment. Note that base 802 of push button key 8 has been pushed within well 36 so that its top is flush with the mouth of well 36. At this lower or second placement location, catch 44 extending from the inside wall of well 36 is engaged to notch 826. Given that the tip of catch 44 is in butting relationship to the base of notch 826, push button key 8 could no longer be moved to the first or higher placement location as shown in FIGS. 10 and 11. In other words, push button key 8 is fixedly maintained at the placement location shown in FIGS. 12 and 13.

To get to that second placement location, as was mentioned earlier, safety lock 10 has to be pushed by the user in a direction toward the back of housing 22 so that it clears the top rim of well 36. At the same time, the user pushes push button key 8 downwards until catch 44 engages notch 826. At that point, as best shown in FIG. 13, the space 822 defined between legs 804 and 806 becomes aligned with the longitudinal axis of housing 22 so that it intersects bore 30. And as space 822 is larger than collar 408, due to the biasing force exerted by spring 6 against surface 410 of collar 408, needle hub 402 is pushed backwards to thereby retract needle 16 within housing 22. As the biasing force of spring 6 dissipates due to it returning to its relaxed state, as needle hub is pushed further such that groove 42 is aligned underneath stopper element 12, base 128 of stopper 12 springs into groove 42, thereby preventing further movement of needle assembly 4. As a result, needle 16 is fixedly retained within housing 22. And as elastic stopper 12 is encased within space 40 of upraised portion 38 of the housing, once mated to groove 42, stopper 12 will remain biasedly mated therewith, thereby preventing needle 16 from escaping out of housing 22.

A second embodiment of the needle device of the instant invention is shown in FIGS. 14–25. Elements for the second embodiment needle device that are the same or similar to those of the first embodiment are labeled the same.

Figure 14:
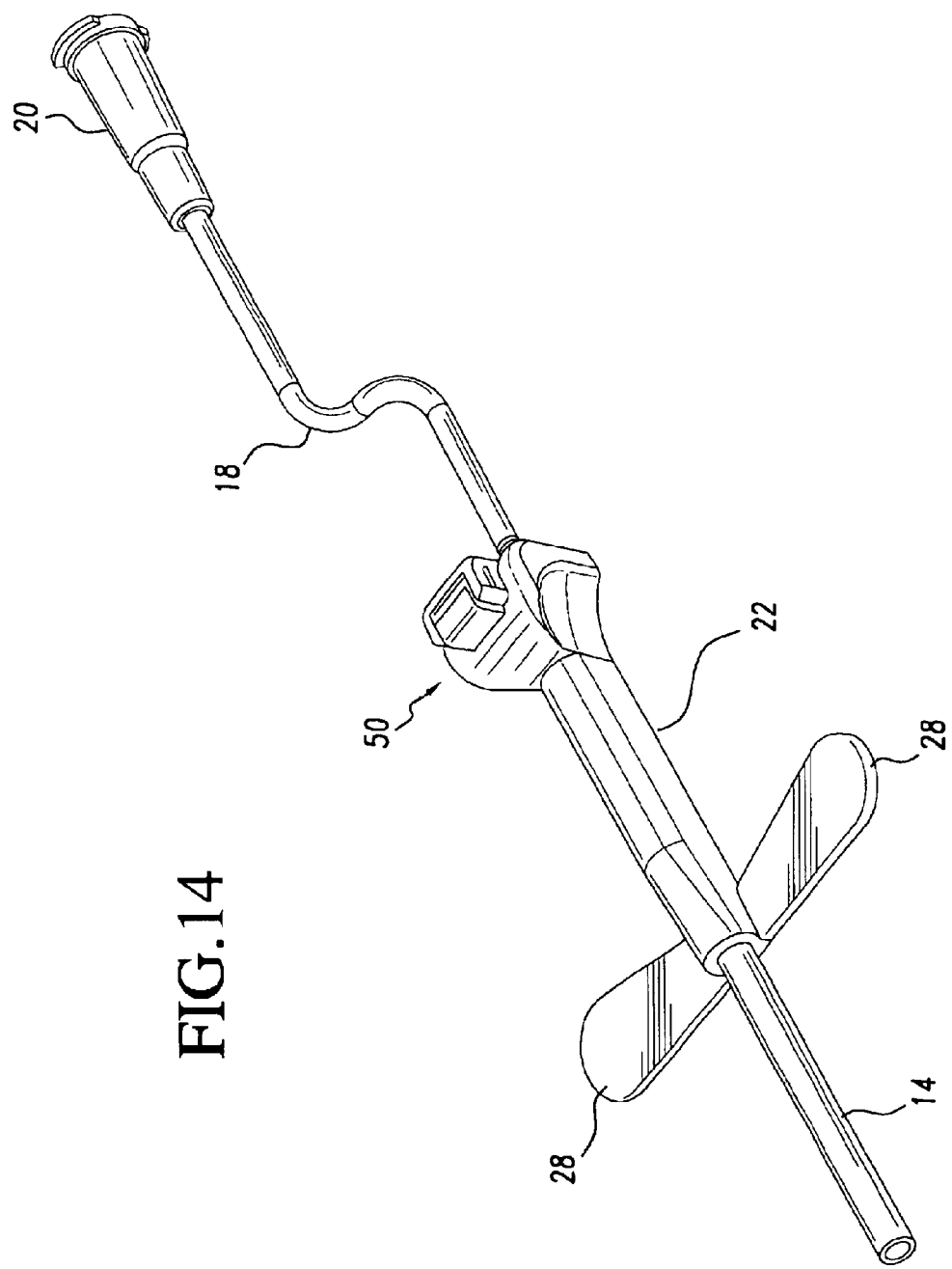
FIG. 14 is a perspective view of a second embodiment of the needle device of the instant invention.
Figure 15:
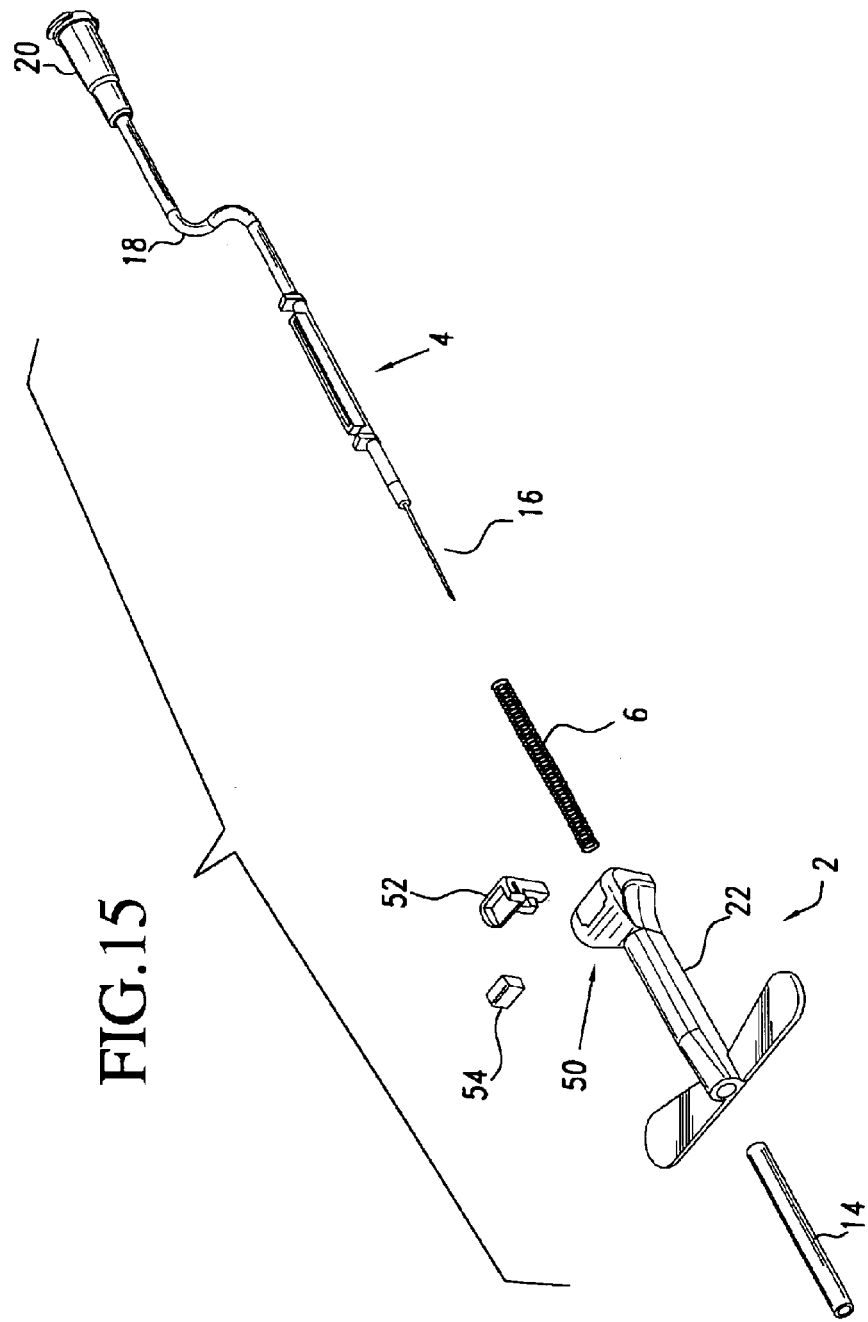
FIG. 15 is an exposed view of the various elements of the needle device of the second embodiment of the instant invention.
Figure 16:
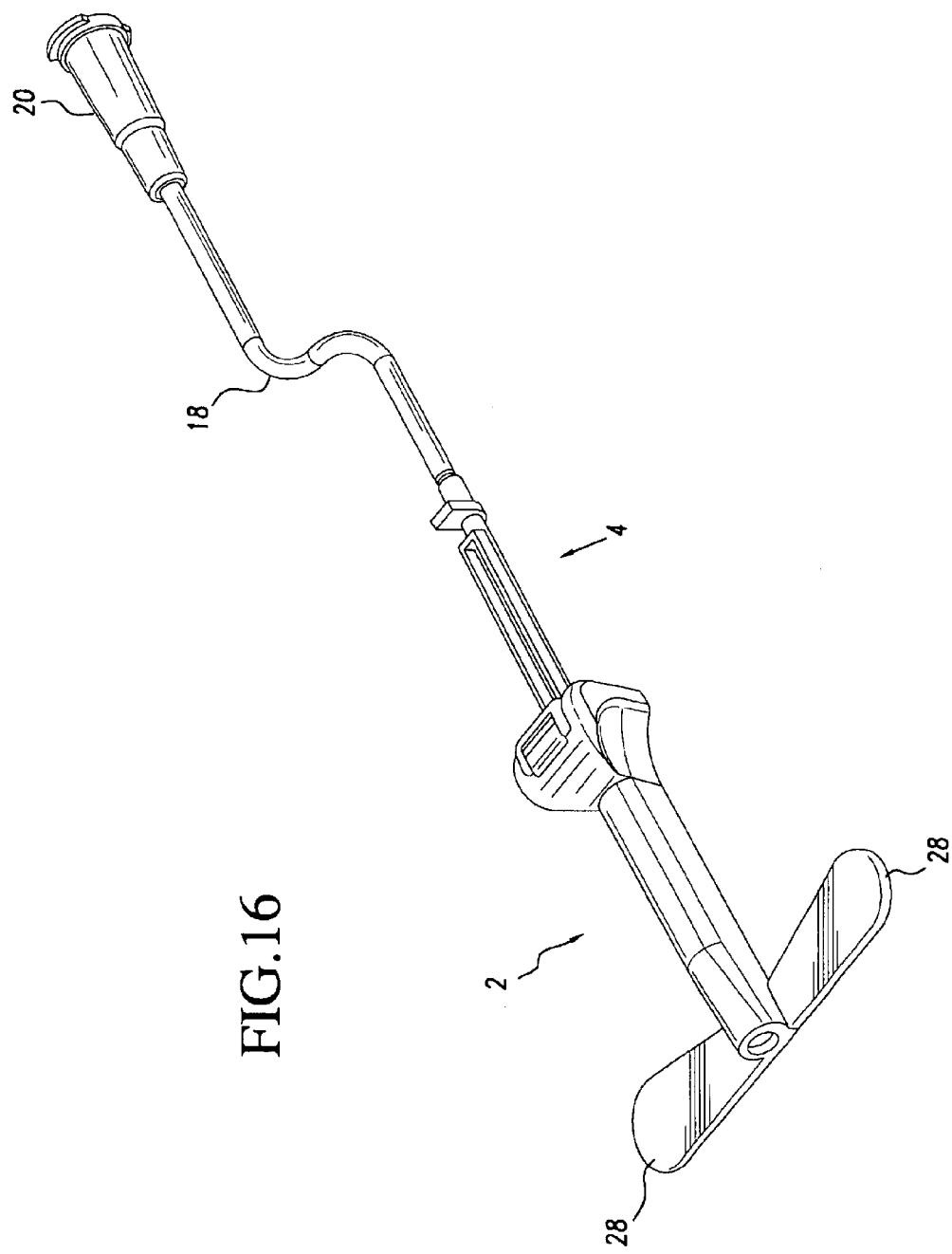
FIG. 16 is a view of the needle having been retracted into the housing for the second embodiment needle device of the instant invention.
Figure 17:
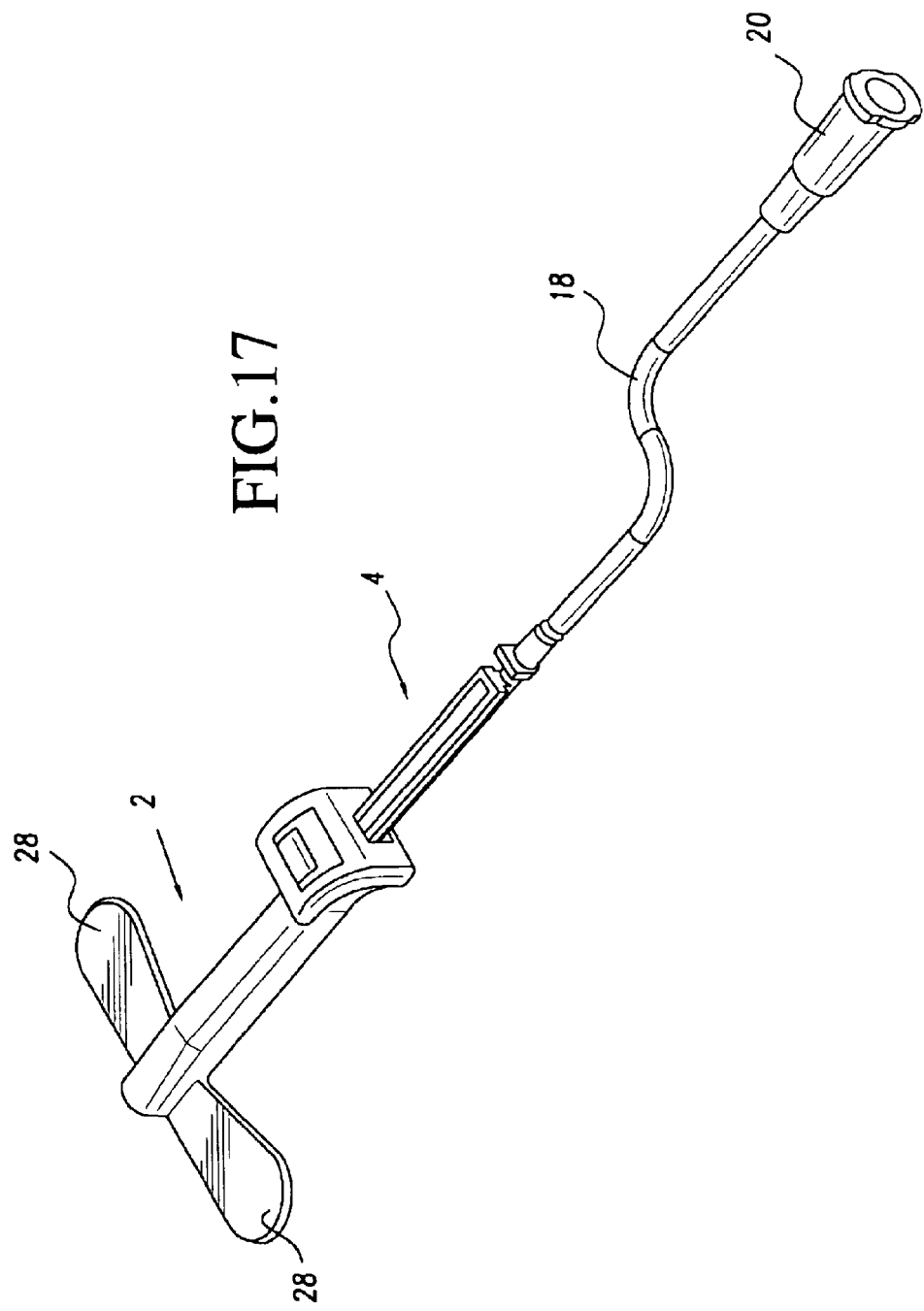
FIG. 17 is a perspective rear view of the needle device of FIG. 16.

The needle device of the second embodiment is similar to the first embodiment needle device except for its push mechanism, its lack of a stopper element, and the portion of the housing that encases the stopper element. In particular, as shown in FIGS. 14, 15 and 17, instead of a well positioned at the front or mid section of the housing into which a push button key is inserted, the second embodiment needle device has at the rear portion of housing 22 an enlarged well portion 50. Fitted to the well of portion 50 is a push mechanism or key 52. A safety lock 54 interacts with push key 52 to ensure that key 52 would not be inadvertently pushed completely into the passage provided by well 50 to automatically retract needle 16 into housing 22.

Figure 18:
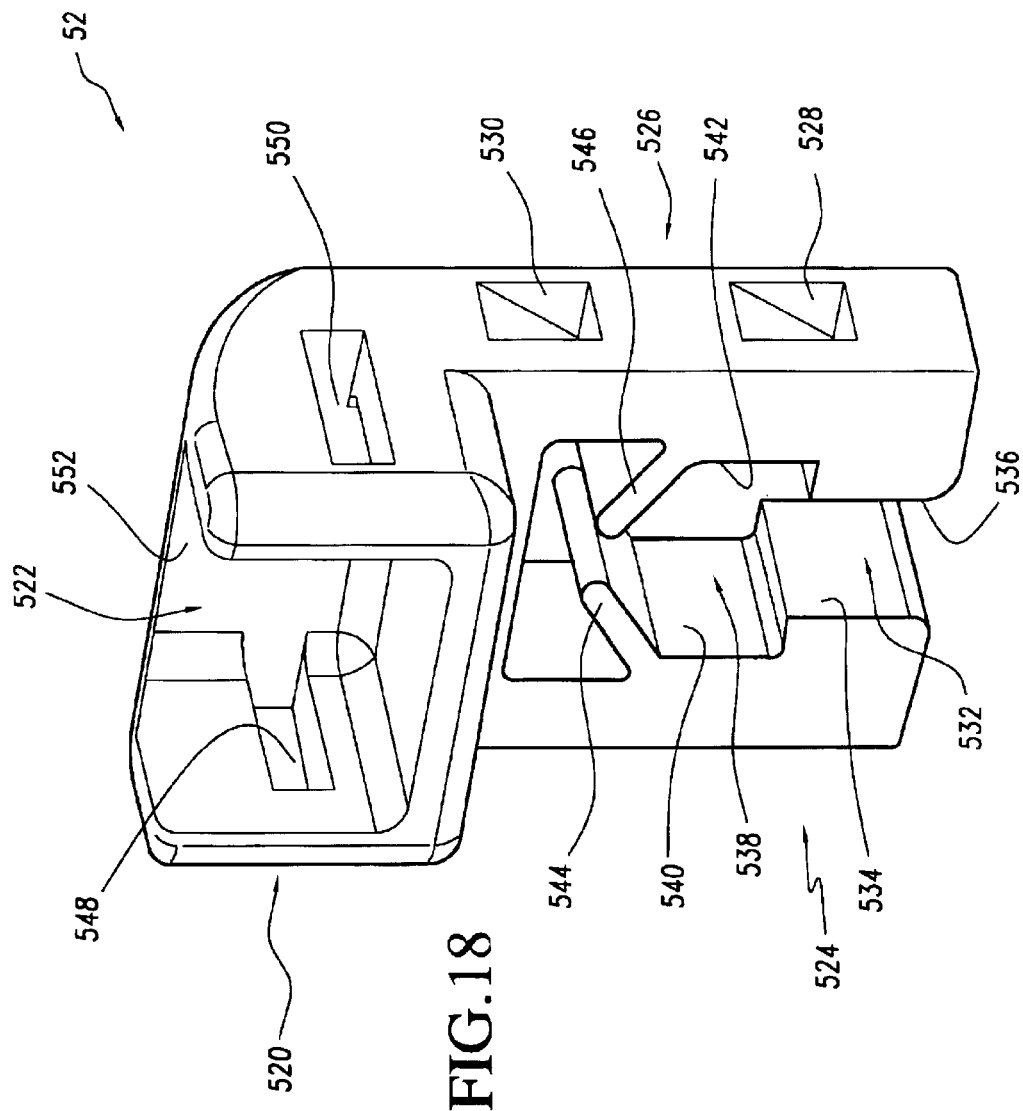
FIG. 18 is the push mechanism of the second embodiment device.
Figure 19:
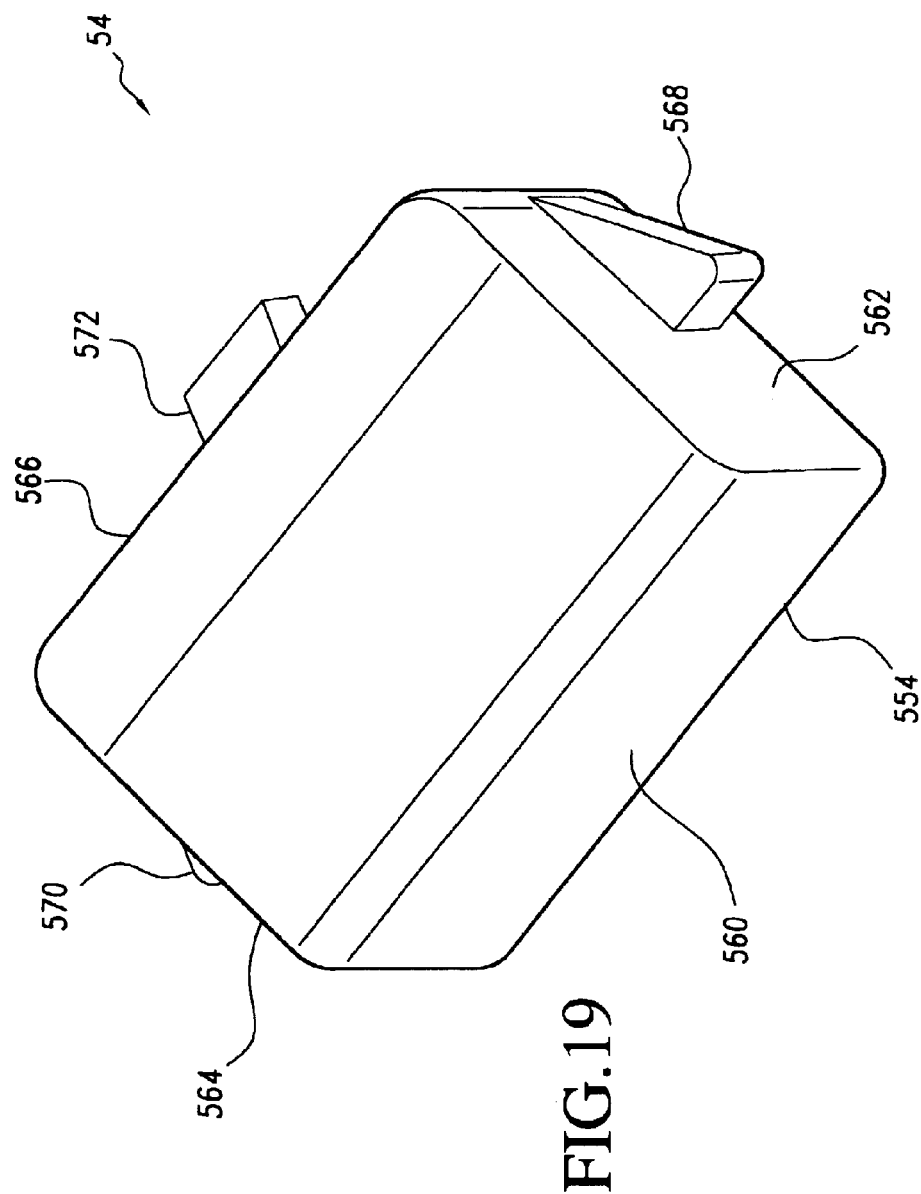
FIG. 19 is the safety stop mechanism for the needle device of the second embodiment.

As shown in FIG. 18, push key 52 has a base or a top portion 520 that includes a void or cavity 522 to which safety lock 54 is fitted. Similar to the push key of the first embodiment, push key 52 of FIG. 18 has two legs 524 and 526. As shown in FIG. 18, on the outside wall of leg 526 there are provided two notches 528 and 530. Each of notches 528 and 530 has a planar base and an incline intersecting therewith to form the notch. Although not shown, similar notches are formed on the outer wall of leg 524.

Similar to the push key of the first embodiment, a non-uniform opening, in the form of different dimensioned spaces, are formed between the opposing inner walls of legs 524 and 526. As shown, at the respective distal ends of legs 524 and 526 there is formed a space 532 defined by converging opposing walls 534 and 536. Another space 538 is defined by the non-converging opposing inner walls 540 and 542 of legs 524 and 526, respectively. For push key 52, there is moreover extending from the opposing inner sidewalls of legs 524 and 526 two extending flaps 544 and 546. The purpose of flaps 544 and 546 is described later.

With respect to the base 520 of push key 52, there is provided at its sidewalls corresponding slots 548 and 550.

Safety lock 54, which may take the form of a plug fitted to cavity 522 of push key 52, has a front surface 560, two side surfaces 562 and 564, and a back surface 566. Extending from the respective side surfaces are inclining extensions 568 and 570. An elastic flap or finger 572 is formed at the back surface 566 of safety lock 54. Similar to the biasing flap of the safety lock of the first embodiment, flap 572 biases against back surface 552 when safety lock 54 is mated to cavity 522. Once inserted to cavity 522, extensions 568 and 570 would engage with slots 550 and 548, respectively, so that safety plug 54 could no longer be removed from base 520 of push key 52.

Figure 20:
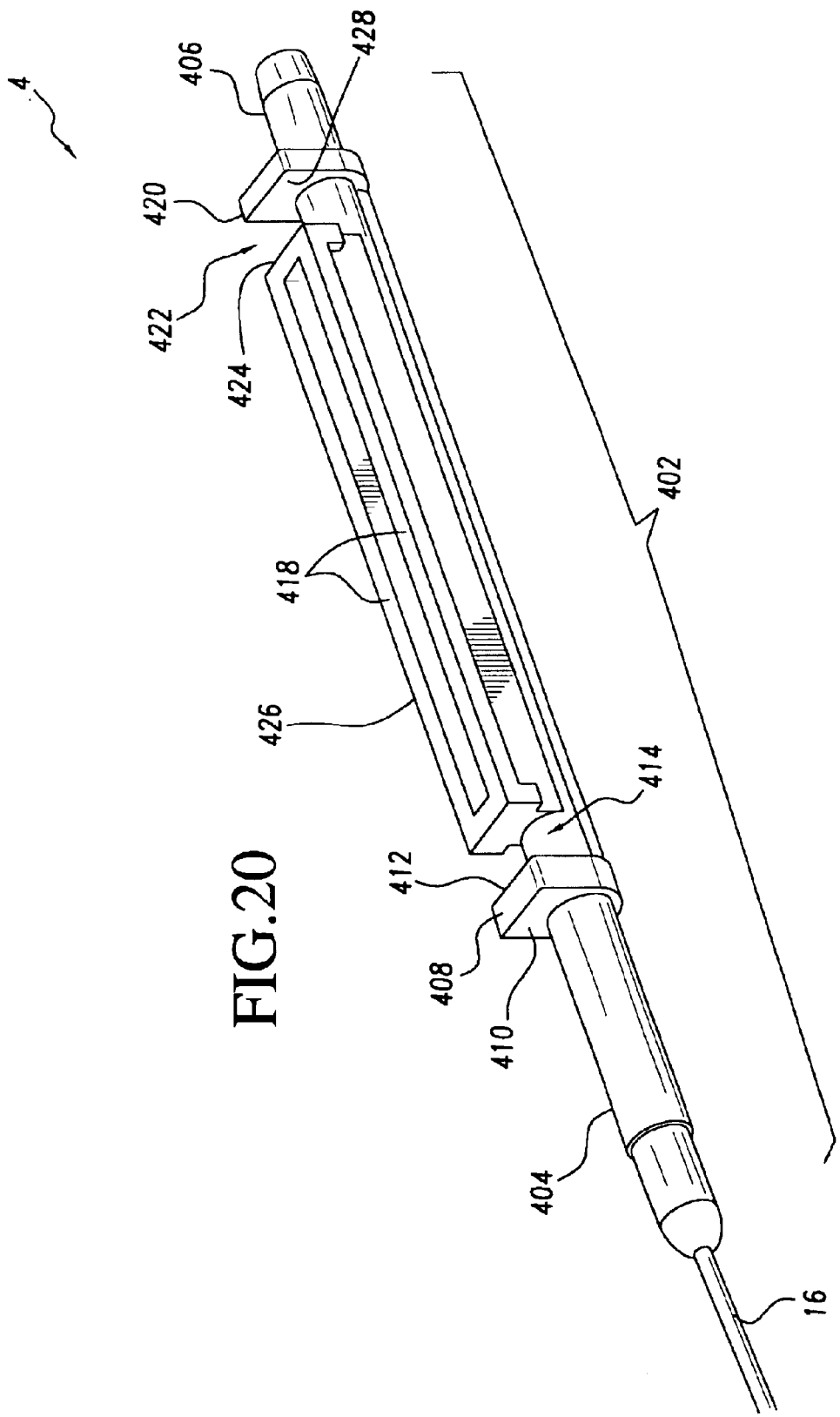
FIG. 20 is a perspective view of the needle assembly of the needle device of the second embodiment.

As shown in FIG. 20, the needle assembly of the second embodiment is substantially the same as the needle assembly of the embodiment shown in FIG. 8, except for the top edges 418 of the needle hub not inclining from the front to the back. Moreover, an additional groove 422 is defined between the rearmost surface 424 of the guide portion 426 of the needle hub and the front surface 428 of the rear rib 420.

Figure 21:
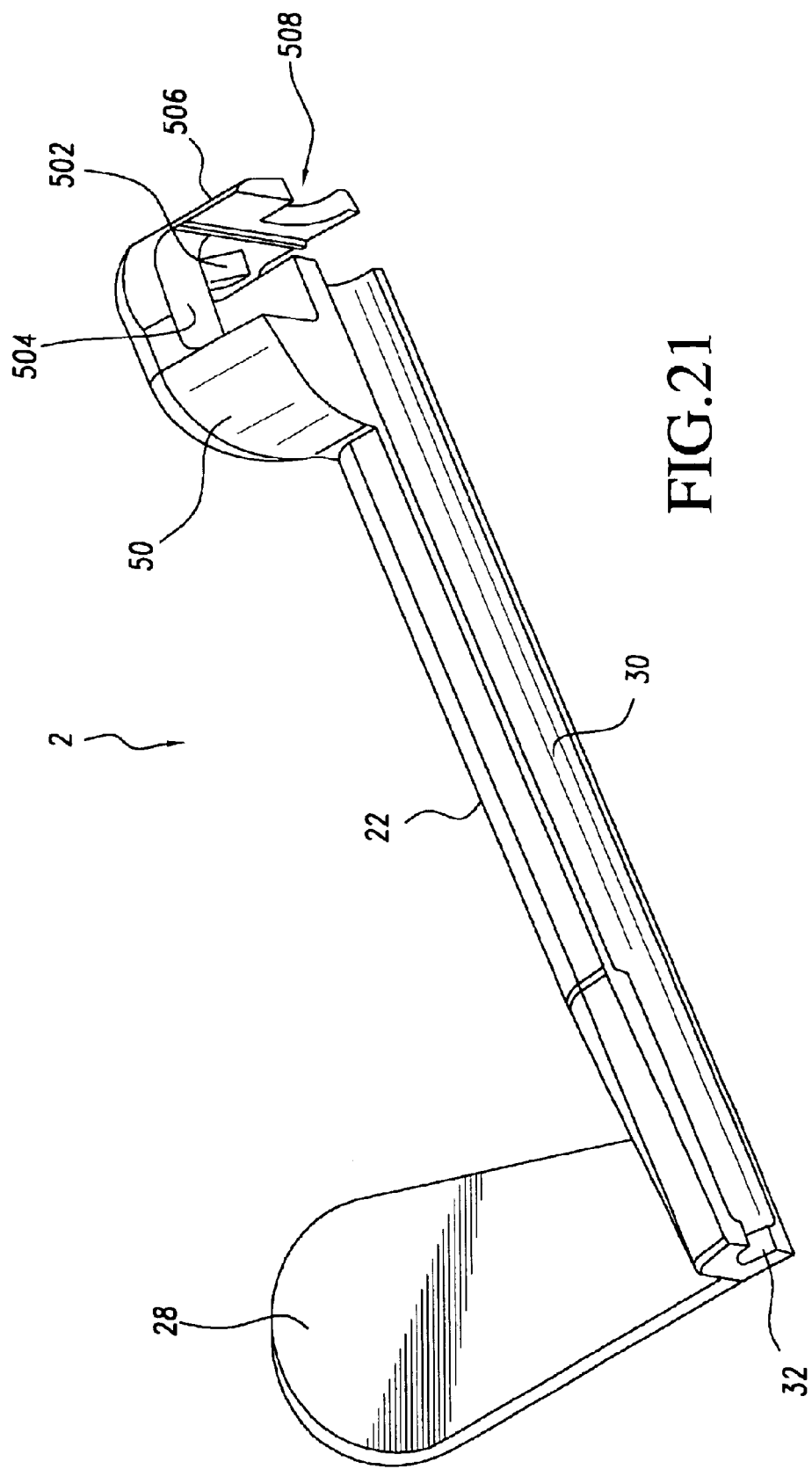
FIG. 21 is a cut-away view of the housing of the second embodiment needle device of the instant invention.

In the cut-away view of housing 2 as shown in FIG. 21, at the well 50 there is provided a catch 502 that coacts with notches 528 and 530 at the outer wall of leg 524 of push key 52. A similar catch 502 is provided on the wall opposing inner wall 504 of well 50. A back wall 506 of well 50 defines an opening 508 that has a dimension that allows guide 426 of needle hub 402 to pass through. As with the first embodiment, opening 32 at the front end of housing 22 enables needle 16 to extend out of housing 22 for use with a patient.

Figure 22:
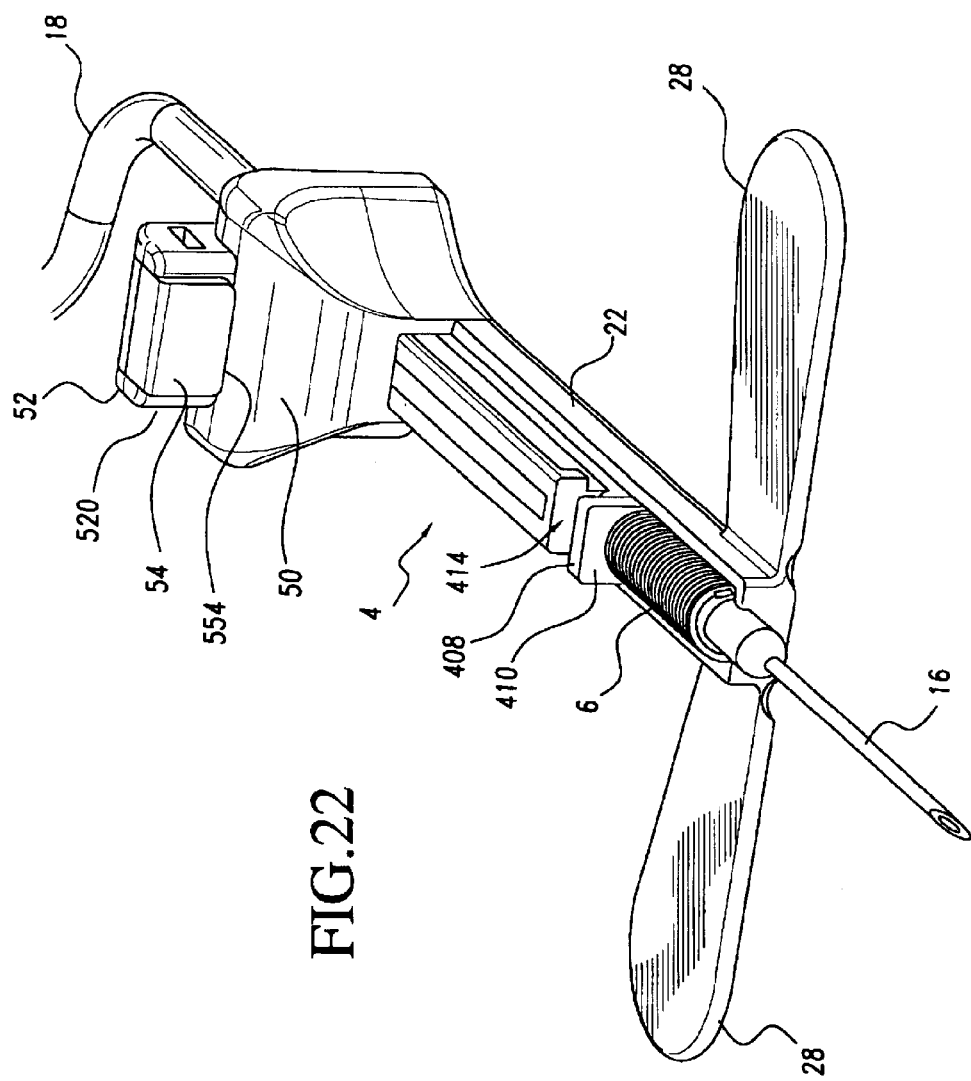
FIG. 22 is a semi cut-away view of the second embodiment of the needle device of the instant invention.
Figure 23:
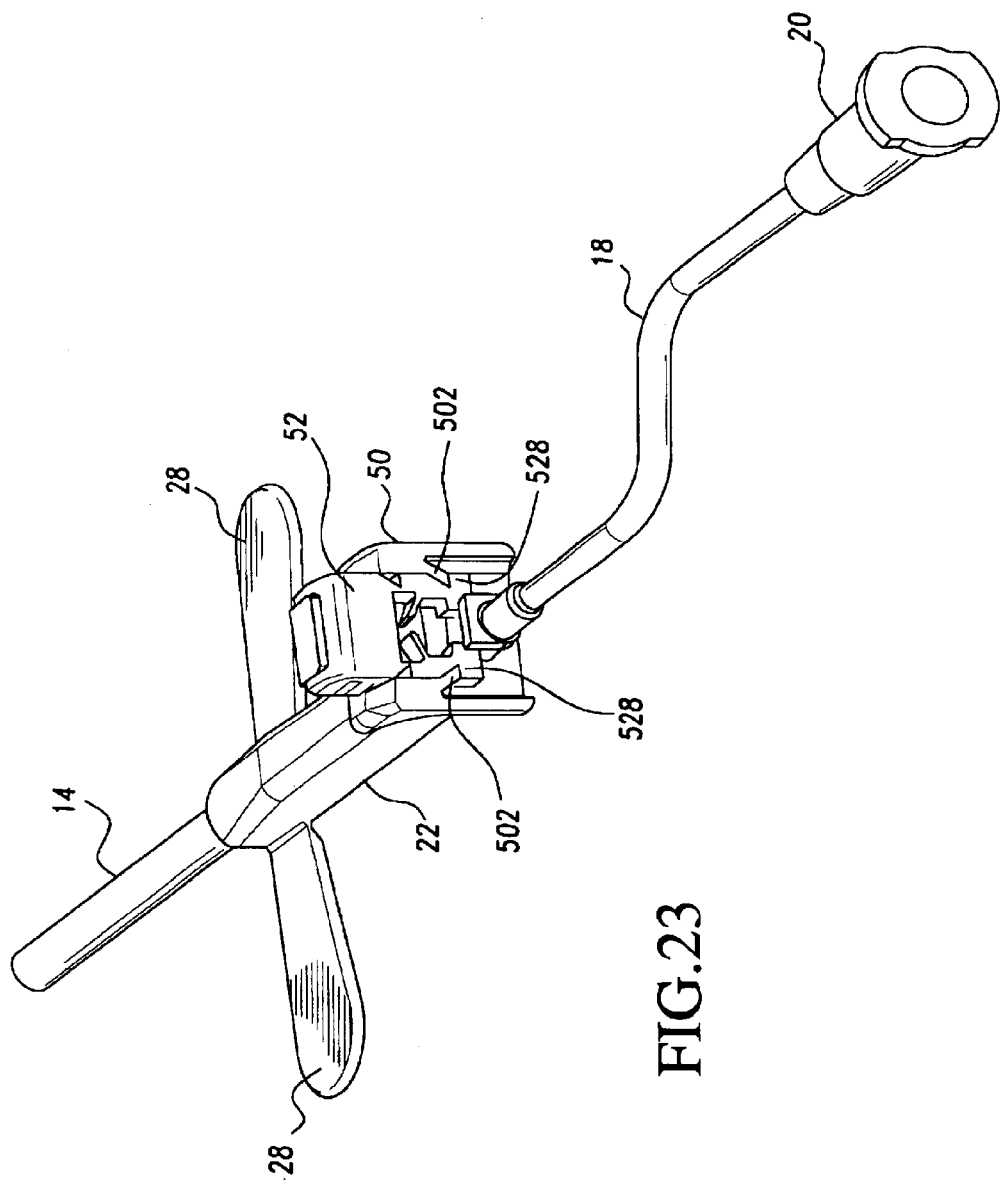
FIG. 23 is a semi cut-away view of the back portion of the second embodiment of the needle device of the instant invention.

The needle device of the second embodiment, before use, is shown in FIGS. 14, 22 and 23. With sheath 14 removed from needle 16, the needle device of the second embodiment of the instant invention is best illustrated by FIG. 22 in which the needle assembly is shown to be maintained at a fixed position relative to housing 22 with needle 16 extending out of opening 32. In this position, the bias spring element 6 is compressed between the inner wall at the front end of housing 22 and front surface 410 of collar 408. Note also that base 520 of push key 52 is positioned above the mouth of well 50. In addition, safety lock 54, due to flap 72 biasing against back wall 552 of push key 52, extends away from push key 52 so that the outermost portion of its underside 554 abuts the top surface of well 50, thereby preventing any inadvertent push down of push key 52 into well 50. As shown in FIG. 23, needle assembly 4 is fixed at the position as shown in FIG. 22 due to the interaction between push key 52 and needle hub 402. In particular, catches 502 extending from the inner walls of well 50 mate with the corresponding notches 528 of legs 524 and 526, so that key 52 is fixed at the placement location as shown in FIG. 23. At that placement location, due to the converging opposed inner walls of the distal ends of legs 524 and 526 mating with groove 522 of needle hub 402, the needle assembly 4 is fixedly held in position in housing 22.

Figure 24:
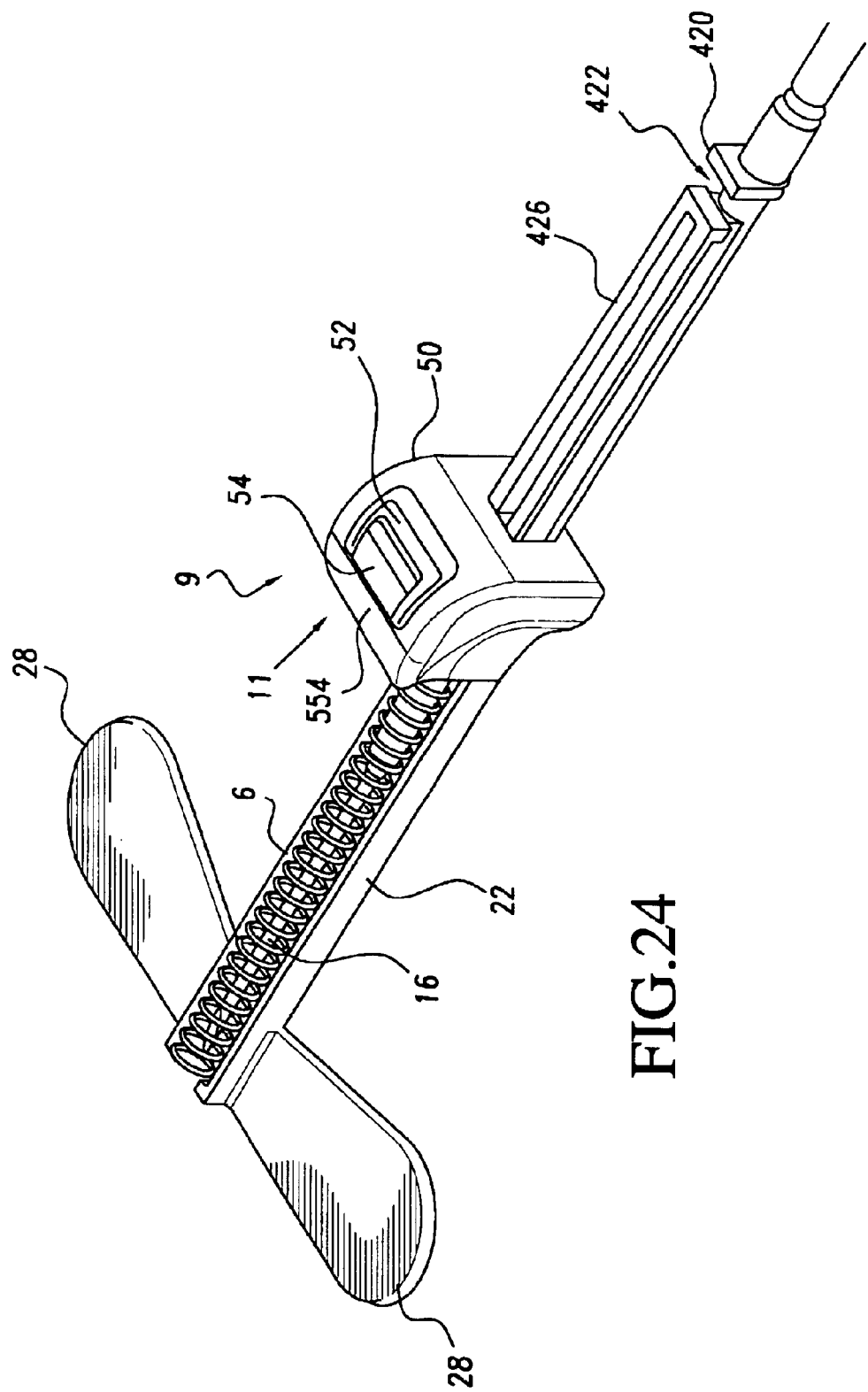
FIG. 24 is a semi cut-away view of the needle device of the second embodiment of the instant invention showing that the needle has been retracted within the housing.
Figure 25:
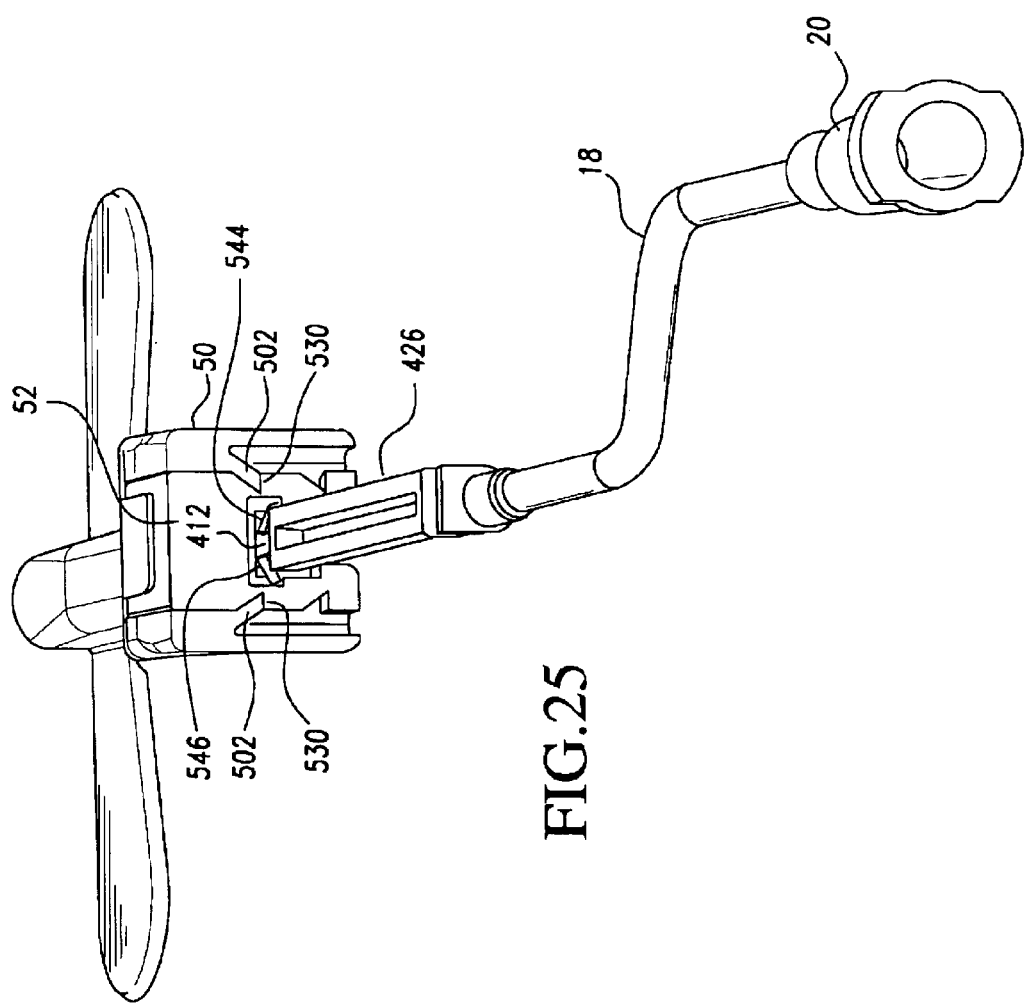
FIG. 25 is a semi cut-away back view of the second embodiment needle device of the instant invention.

As shown in FIGS. 24 and 25, after the needle 16 has been withdrawn from the patient, the user would push safety lock 54 in the direction as shown by directional arrow 11 so that its underside 554 clears lip 554 of well 50. At the same time or shortly thereafter, the user would push key 52 down along the direction as indicated by directional arrow 9 so that key 52 is positioned in the placement location whereby the tops of key 52 and safety lock 54 are flush with the mouth of well 50.

As best shown in FIG. 25, at the placement location whereby key 52 is pushed flush with the top of well 50, catches 502 extending from the inner walls of well 50 engage notches 530 at the outer wall of legs 524 and 526. As a consequence, space 540 intersects bore 30 and becomes aligned with guide 426 of the needle hub. As space 538 has a dimension that is slightly larger than guide 42, due to the biasing force acting against rib 408 by spring 6, the needle assembly is pushed rearwards until guide 426 is positioned as shown in FIGS. 24 and 25, and needle 16 retracted into housing 22. As guide 426 fully passes though space 538, flaps 544 and 546 come into abutting relationship with rear surface 412 of collar 408, thereby stopping any further backward movement of the needle assembly. Further, due to the tendency to return to the natural position due to their elastic nature, flaps 544 and 546 become mated to groove 414 of the needle hub to fixedly retain the needle assembly relative to housing 22, thereby lockingly retaining needle 16 within housing 22.

Figure 31:
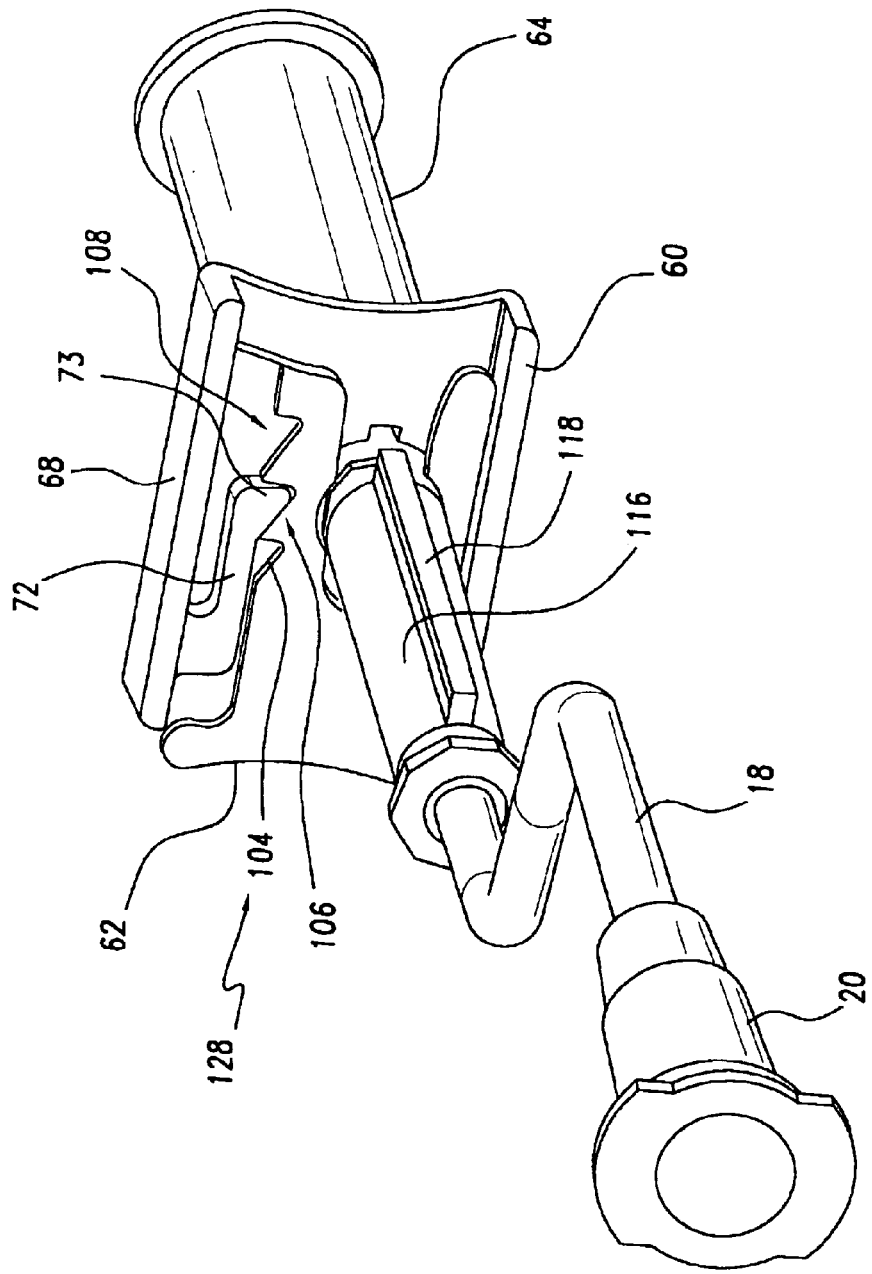
FIG. 31 illustrates the needle device of the third embodiment of the instant invention, with the sleeve being exposed to show the interaction between the catch at the sleeve and the teeth at the key.
Figure 32:
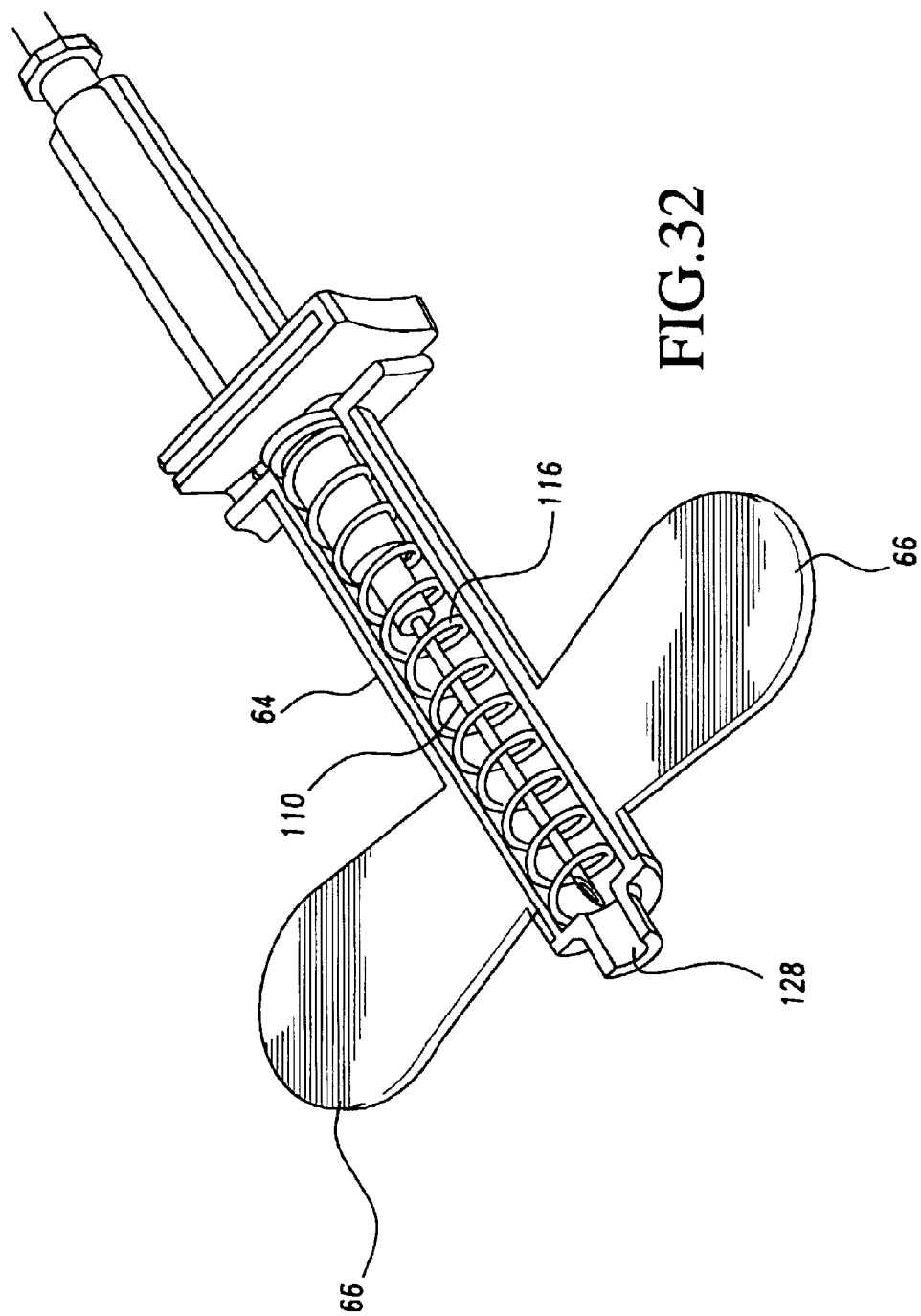
FIG. 32 is a semi cut-away view showing the needle having been retracted within the housing for the third embodiment needle device of the instant invention.

A third embodiment of the needle device of the instant invention is discussed with reference to FIGS. 26–32. For this embodiment, instead of a push button fitting inside a well upraised from the body of the housing, the passage to the bore of the housing is provided by means of a sleeve 60, and the coacting key 62 slidably fitted thereinto. As best shown in FIG. 29, sleeve 60, with its rear wall not shown, is integrally connected to the rear portion of a needle housing 64. As shown in FIGS. 31 and 32, wings 66 are attached to the sides of housing 64. Sleeve 60 is formed by two parallel walls, with the back wall not shown, sandwiched by a top 68 and a base 70. Integrated to top 68 is a catch 72 that, due to its construction, is capable of flexing upwards to give way when contacted at its incline surface 74. An opening 76 is formed at front wall 78 to provide a passage to the interior bore of housing 64.

Figure 26:
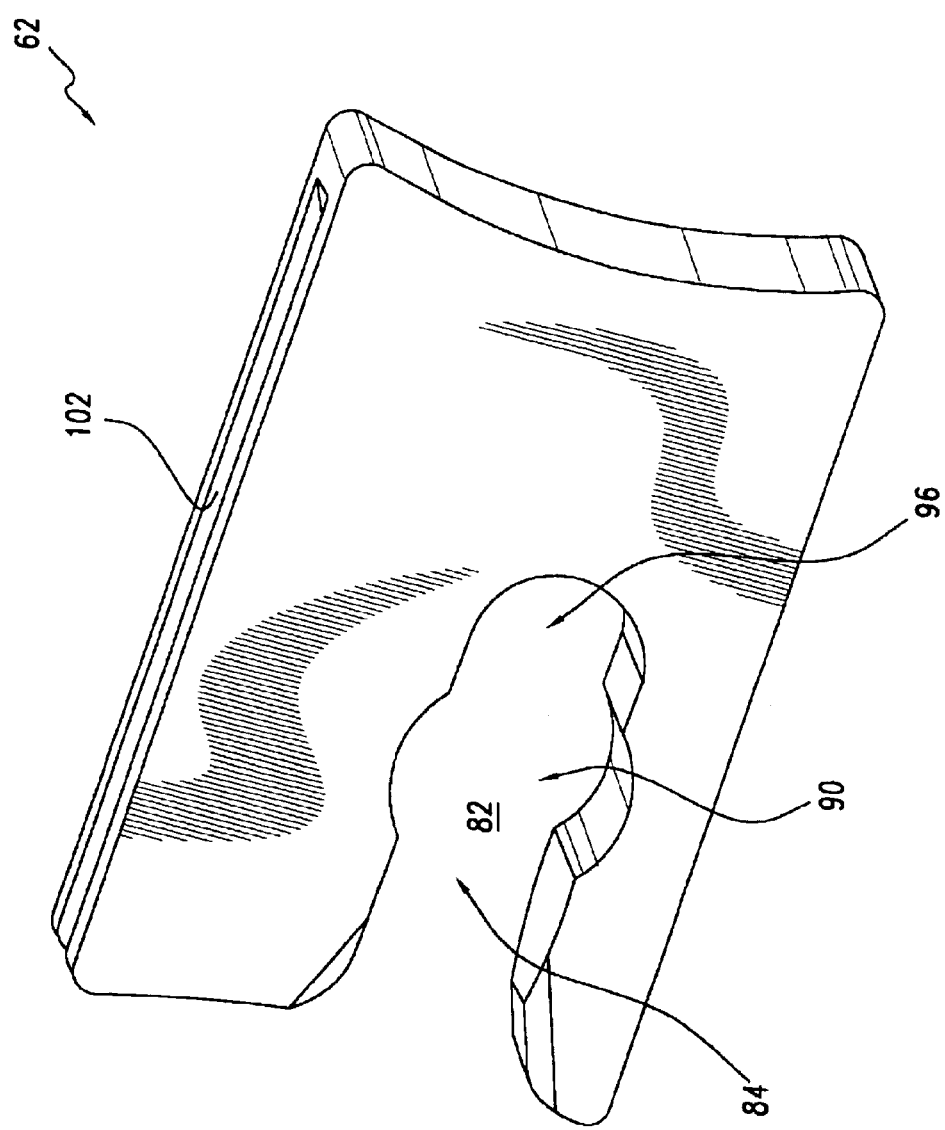
FIG. 26 illustrates the push mechanism of a third embodiment of the needle device of the instant invention.
Figure 27:
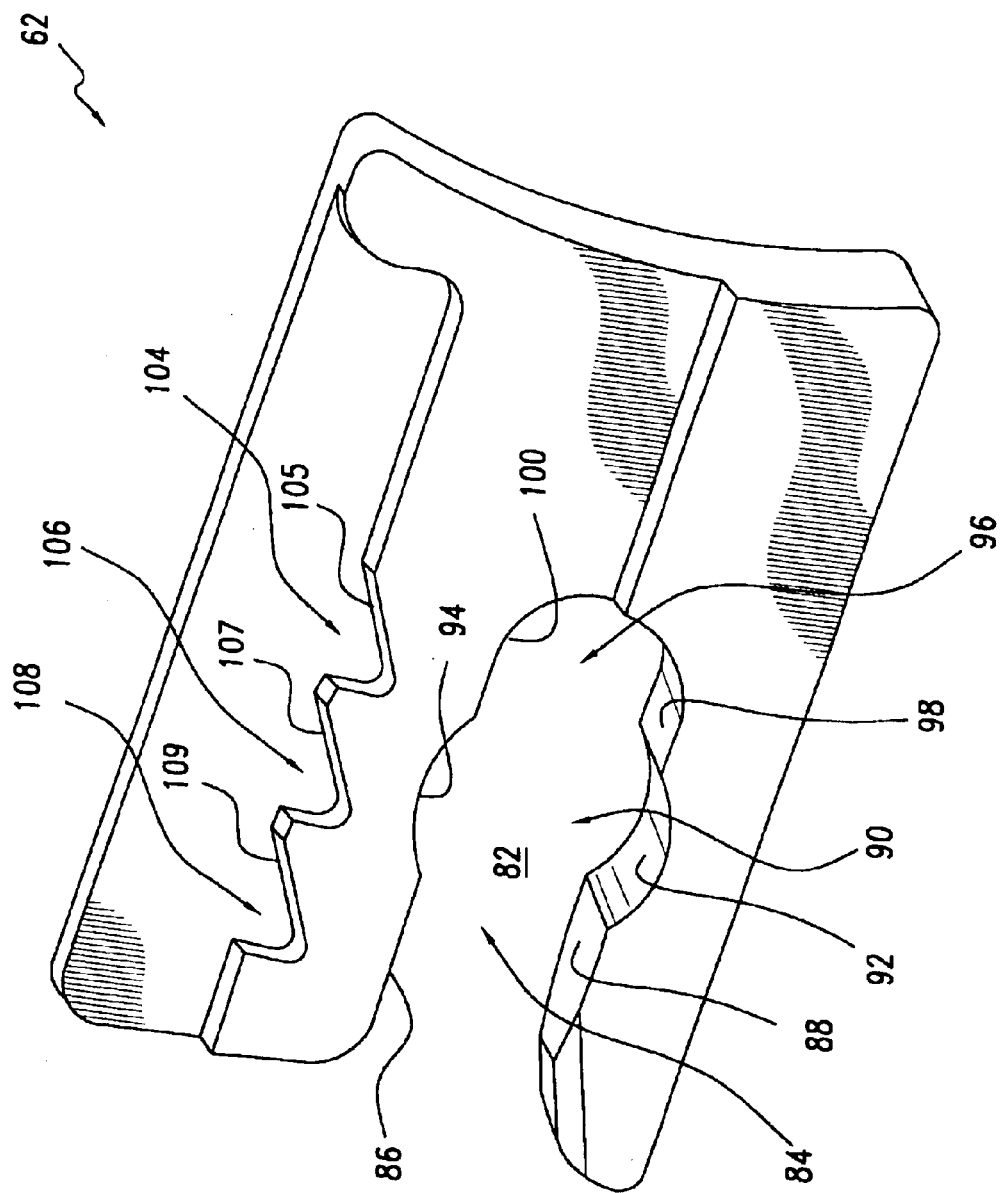
FIG. 27 illustrates the sleeve of the third embodiment needle device of the instant invention.

Key 62, which is slidably inserted to sleeve 60 in the direction as indicated by directional arrow 80, is shown in FIGS. 26 and 27. Key 62 has a non-uniform opening 82 that includes spaces of different dimensions. As shown, opening 82 comprises a first space defined by its opposed interior wall portions 86 and 88. A second space 90 is defined by semi-circular opposing inner walls 92 and 94. There is yet a further space 96 which is defined by opposing inner walls 98 and 100. At the upper portion of key 62 there is a slot 102 formed with defined one-way notches 104, 106 and 108. These notches are each formed to fittingly mate with tooth 73 of catch 72, with incline 74 of catch 72 adaptable to fittingly contact the respective inclines 105, 107 and 109 of notches 104, 106 and 108.

Figure 28:
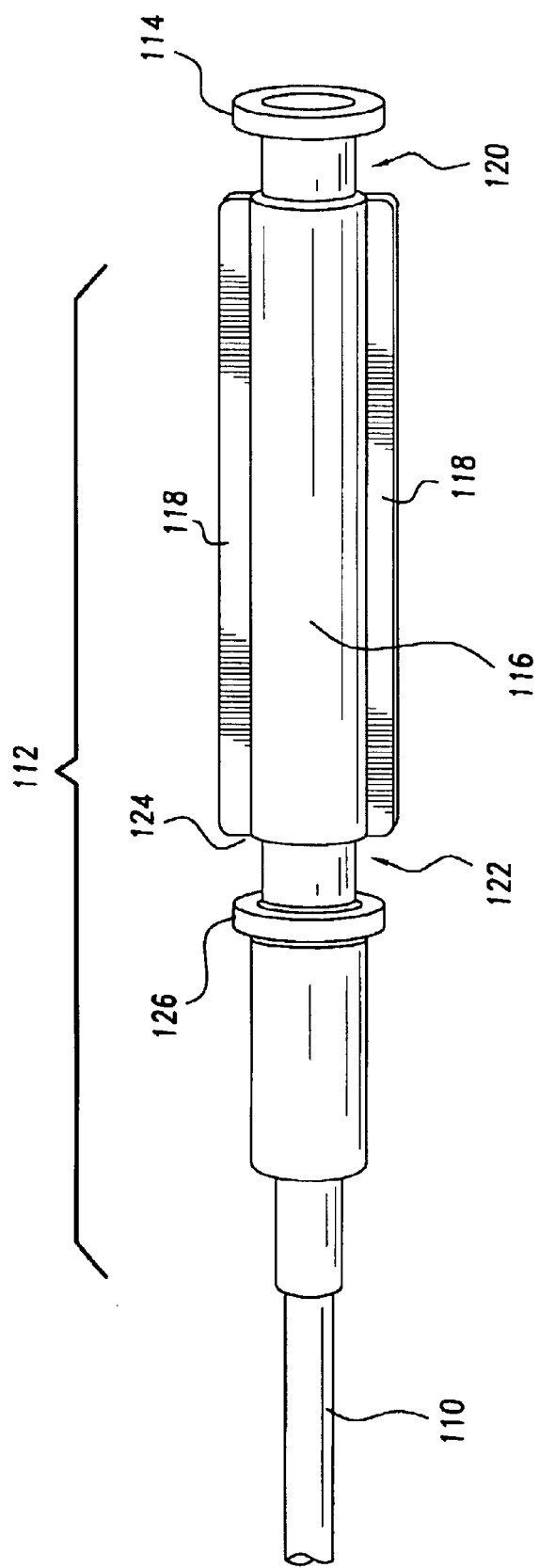
FIG. 28 shows the needle assembly of the third embodiment needle device of the instant invention.
Figure 29:
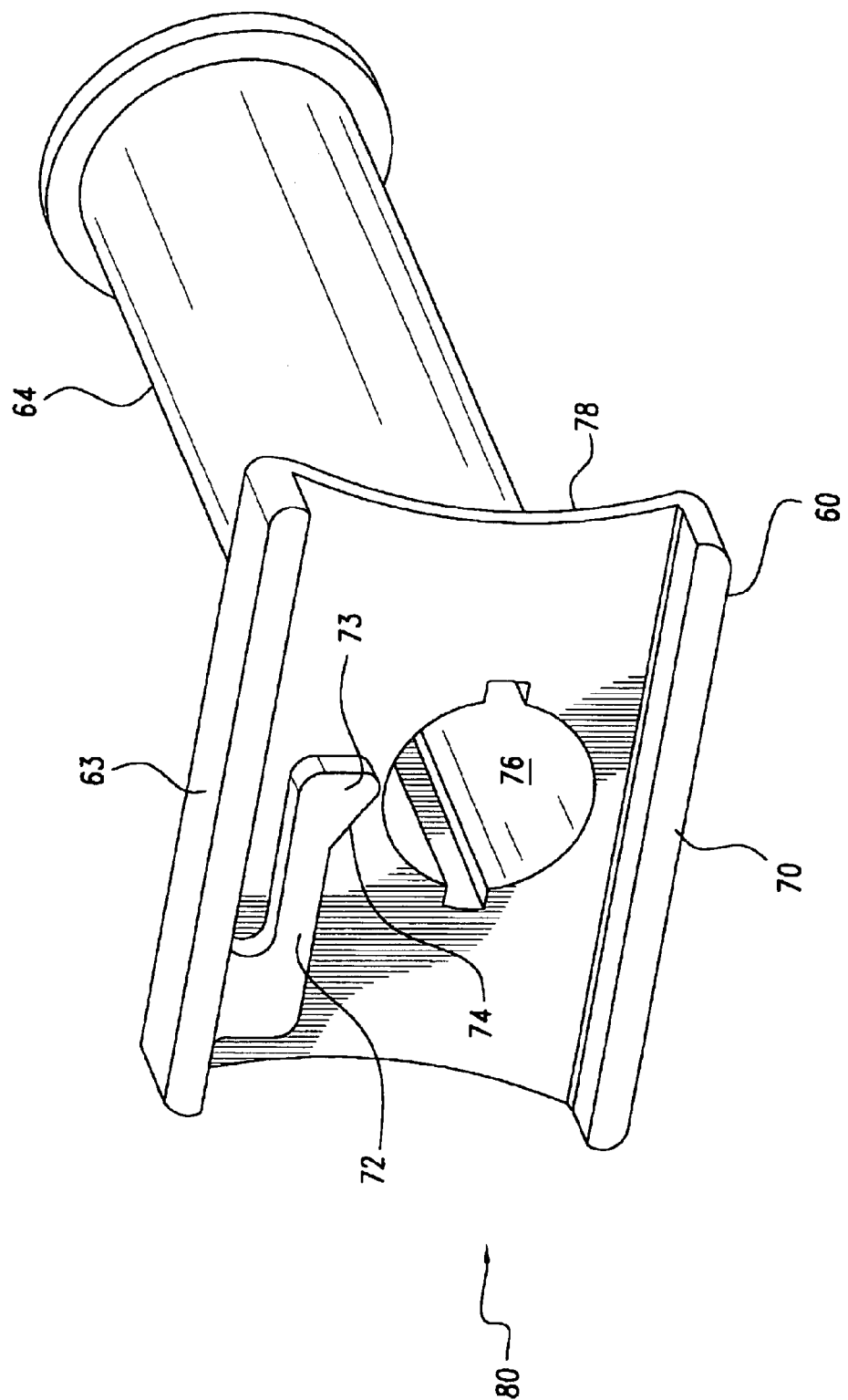
FIG. 29 is a semi cut-away back view of the housing of the third embodiment needle device of the instant invention.

The needle assembly of the third embodiment of the needle device of the instant invention is shown in FIG. 28 to have a needle 110 extending from a needle hub 112. Connected to the other end of needle hub 112 is a luer 114 that is connectable to an infusion line 18. Needle hub 112 has a guide portion 116 that has two flanges 118 extending longitudinally therealong. A first groove 120 is formed between the rear end of guide portion 116 and the front surface of connector 114. A second groove 122 is formed between the front end 124 of guide portion 116 and a rib or collar 126.

Figure 30:
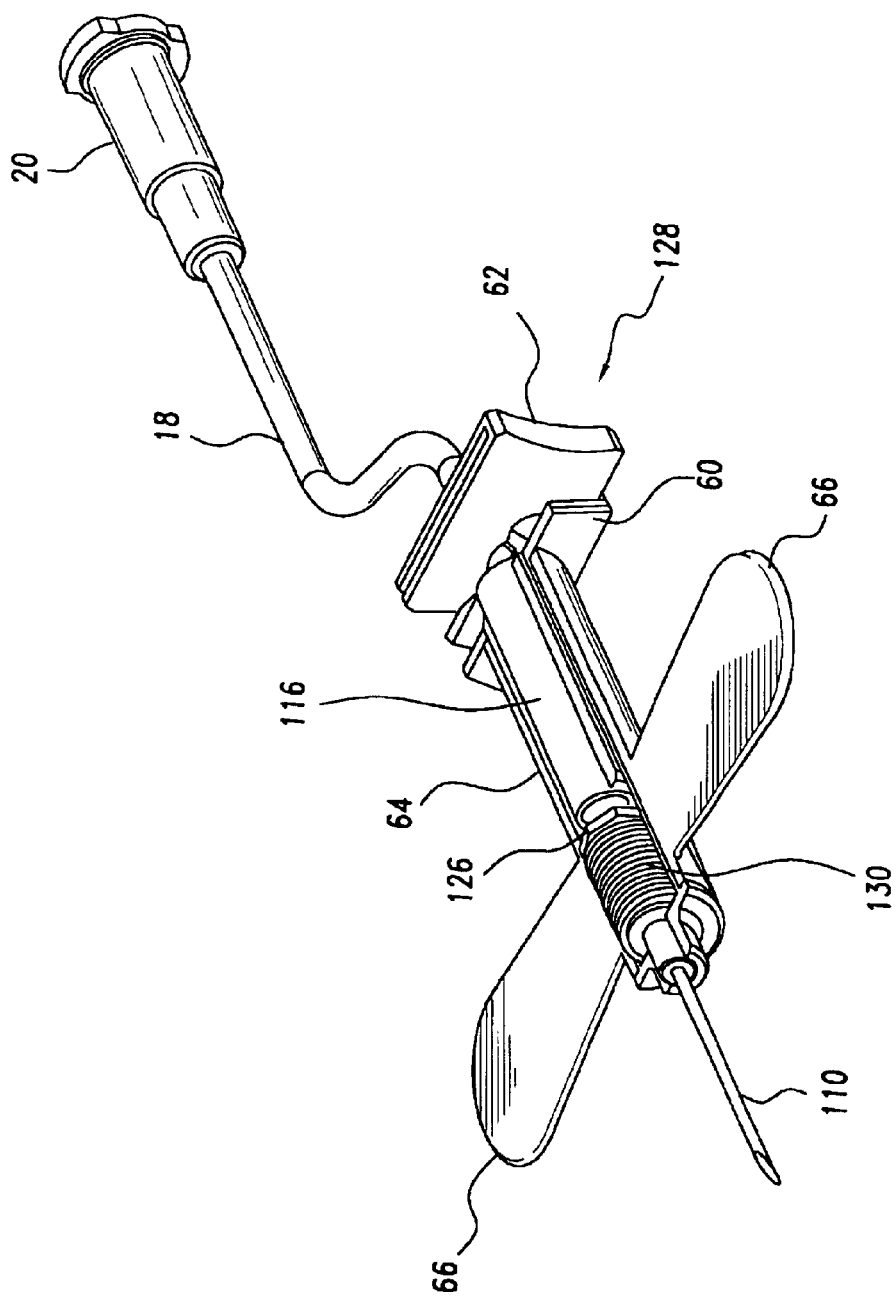
FIG. 30 is a semi cut-away front view of the third embodiment needle device of the instant invention.

FIG. 30 shows the positioning of the needle assembly vis-a-vis housing 64 with needle 110 extending from the front opening 128 of needle housing 64. A bias element in the form a spring 130 is compressed between the inner surface of the front end of syringe 64 and the front surface of collar 126. The needle assembly, particularly guide portion 116, is maintained in the position as shown in FIG. 30 by key 62 being positioned at the shown placement location. At the placement location of FIG. 30, the distal portion of key 64, as defined by space 84, intersects the bore of needle housing 64 so that the converged opposing inner walls of key 62 that define space 84 are mated to groove 120. Although not shown, but with reference to FIGS. 27, 29 and 31, it should be appreciated that tooth 73 of catch 72 is mated to notch 108 when key 62 is fitted to sleeve 60 at the placement location shown in FIG. 30. With key 62 being positioned as such relative to sleeve 60, the user can insert needle 110 into a patient for either infusion or withdrawing of blood.

Once needle 110 is withdrawn from the patient, to retract the now contaminated needle 110 into housing 64, the user would push key 62 in the direction as shown by directional arrow 128. Incline 107 of notch 106 would accordingly abut against incline 74 of catch 72 so that tooth 73 is flexed toward top 68 until key 62 is positioned at the placement location as shown in FIG. 31. At that point, tooth 74 would fittingly mate with notch 106 so that no movement in the direction reverse to that of directional arrow 128 could take place, due to the interaction of the front surface of tooth 73 butting against the flat front of notch 106.

When positioned at the placement location as shown in FIG. 31, space 90 of opening 82 becomes aligned with the bore of needle housing 64. And since space 90 is configured to have a larger dimension than guide portion 116 of needle hub, due to the biasing force exerted by spring 126, the needle hub is pushed backwards to retract needle 110 into needle housing 64, as shown in FIG. 32. Thereafter, to fixedly retain needle 110 within housing 64, key 62 is pushed further per directional arrow 128 so that tooth 73 mates with notch 104. At that placement location, since space 96 is aligned with the longitudinal axis of needle housing 64, it mates with groove 122. And since no reverse movement of key 62 is possible due to the abutting relationship of tooth 73 with notch 104, needle 110 is fixedly retained within housing 64.

It should be appreciated that the present invention is subject to many variations, modifications, and changes in detail. Accordingly, it is the intention of the inventor that all matter described throughout this specification and shown in the accompanying drawings be interpreted as illustrative only and not in a limiting sense. The invention is intended therefore be limited only by the spirit and scope of the hereto appended claims.

What is claimed is:

1. A needle device, comprising:
   a housing having a pair of wings, a first end with a first opening and a second end with a second opening;
   a needle assembly having a needle attached to a needle hub slidably fitted within said housing, the needle extendable through said first opening and said needle hub passable through said second opening;
   a bias element inside said housing for applying a biasing force against said needle hub towards said second end;
   a key movably fitted to said housing at a first placement along a plane orthogonal to the longitudinal axis of said housing for maintaining said needle assembly in a first position relative to said housing whereby the needle is extended out of said first opening, said key actuable to a second placement along said plane orthogonal to the longitudinal axis of said housing to allow the needle to be retracted into said housing due to said needle assembly being biased by said bias means; and
   a safety lock element coacting with said key and ordinarily acting against a portion of said housing to prevent inadvertent actuation of said key from said first placement to said second placement.

2. The needle device of claim 1, further comprising:
   a stopper positioned at the second end of said housing having a portion that continuously biases against said needle hub and coacts against a collar of said needle hub to prevent said needle hub from completely passing out of said second opening when the needle is retracted into said housing.

3. The needle device of claim 1, wherein said key comprises a base with two legs extending therefrom, the inside walls of said legs having respective opposed potions that converge towards each other; and
   wherein said needle hub comprises a longitudinal body that has a collar that abuts against the converged opposed portions of said legs when said key means is at said first placement so that said needle assembly is maintained at said first position for extending the needle out of the first opening of said housing.

4. The needle device of claim 1, wherein said housing has an upraised well formed at said first end, and wherein said key comprises a base configured to fit into said well, the outside wall of each of said legs of said base having a notch that coacts with a catch from the inside wall of said well to maintain the converged opposed portions of said legs in abutting relationship with said collar when said key is at said first placement, at least a portion of said base being located above the mouth of said well at said first placement.

5. The needle device of claim 1, wherein said key comprises a base having a cavity whereinto said safety lock element is biasedly fitted, said safety means comprising a lock button movable into the cavity of said base, said lock button preventing downward movement of said base if it is not in the cavity of said base, so that before said key is movable to said second placement, said lock button needs to be moved into the cavity of said base.

6. The needle device of claim 1, wherein said bias element comprises a spring.

7. The needle device of claim 2, further comprising:
a groove formed on said needle hub adjacent said collar;
wherein said stopper falls into said groove and abuts against said collar when the needle is retracted into said housing when said key is moved to the second placement.

8. The needle device of claim 4, wherein each of said legs has a second notch that coacts with said catch from the inside wall of said well when said key is at said second placement, the interaction between said second notch and said catch preventing said base from being moved back to said first placement.

9. A needle apparatus, comprising:
a housing having a pair of wings, a first end with a first opening and a second end with a second opening, a bore extending longitudinally along said housing, a passage orthogonal to the longitudinal axis of said housing in communication with the bore of said housing;
a needle assembly having a needle attached to a needle hub slidably fitted within said housing, the needle extendable through said first opening and said needle hub passable through said second opening;
a bias element inside said housing for applying a biasing force against said needle hub towards said second end;
a key mechanism movably fitted to said passage of said housing, said key mechanism being movable to at least a first placement location and a second placement location relative to said housing, said key mechanism having at least two apertures of different dimensions, one of said apertures having a dimension that prevents the movement of said needle hub to maintain the extension of the needle out of said first opening of said housing, the other of said apertures having a dimension that allows said needle hub to pass through, the movement of said key mechanism being substantially orthogonal to the longitudinal axis of said housing; and
a safety element fitted to said key mechanism and movable in a direction transverse to the movement of said key mechanism to prevent said key mechanism from being inadvertently moved.

10. The needle apparatus of claim 9, wherein said passage comprises a sleeve at the second end of said housing, and
wherein said key mechanism comprises a key slidable in said sleeve having at least two teeth each engageable with a catch at said sleeve so that said one aperture intersects the bore of said housing when said key is at said first placement location and a first of said teeth engages said catch, and wherein said other aperture intersects the bore of said housing when said key is moved to said second placement location, a second of said teeth engaging said catch when said key is at said second placement location, the teeth being one way teeth to prevent said key from being moved from said second displacement location back to said first displacement location once said key has been moved form said first placement location to said second placement location.

11. A needle apparatus, comprising:
a housing having a first end with a first opening and a second end with a second opening, a bore extending longitudinally along said housing, a passage orthogonal to the longitudinal axis of said housing in communication with the bore of said housing;
a needle assembly having a needle attached to a needle hub slidably fitted within said housing, the needle extendable through said first opening and said needle hub passable through said second opening;
a bias element inside said housing for applying a biasing force against said needle hub towards said second end; and
a key mechanism movably fitted to said passage of said housing, said key mechanism being movable to at least a first placement location and a second placement location relative to said housing, said key mechanism having at least two apertures of different dimensions, one of said apertures having a dimension that prevents the movement of said needle hub to maintain the extension of the needle out of said first opening of said housing, the other of said apertures having a dimension that allows said needle hub to pass through, the movement of said key mechanism being substantially orthogonal to the longitudinal axis of said housing;
wherein said passage comprises a well upraised from said housing, and wherein said key mechanism comprises a button fitted to said well, said button comprising a base having two legs extending therefrom to form said apertures, said one aperture intersecting the bore of said housing when said button is at said first placement location and said other aperture intersecting the bore of said housing when said button is at said second placement location, the outside wall of each of said legs having a notch that engages with a catch from the inside wall of said well to maintain said one aperture in place to abut a collar of said needle hub when said button is at said first placement location, a portion of said button being located above the mouth of said well at said first placement location.

12. The needle apparatus of claim 11, wherein said button is pushed into said well so that the top of said button is substantially flush with the top of said well when said button is moved to said second placement location, and wherein said other aperture is positioned in alignment with the bore of said housing at second placement location to enable said needle hub to pass thereby retracting the needle into said housing.

13. The needle apparatus of claim 12, further comprising:
flaps extending from the inside opposing walls of said legs toward each other for preventing the needle from further extending out of said first opening once it has been retracted into said housing.

14. The needle apparatus of claim 11, wherein said button has an exposed cavity, further comprising:
a plug biasedly fitted to said cavity, said plug movable between a position that prevents said button from being moved away from said first placement location and a position within said cavity for enabling said button to be moved to said second placement location.

15. The needle apparatus of claim 9, further comprising:
a stopper positioned at the second end of said housing having a portion that continuously biases against said needle hub and coacts against a rib of said needle hub to prevent said needle hub from completely passing out of said second opening when the needle is retracted into said housing.

16. The needle apparatus of claim 9, wherein said needle apparatus is an IV device.

17. The needle apparatus of claim 9, wherein said bias element comprises a spring.

18. A butterfly needle assembly, comprising:
a housing having a pair of wings, a first end with a first opening and a second end with a second opening, a bore extending longitudinally along said housing, a passage orthogonal to the longitudinal axis of said housing in communication with the bore of said housing;
a needle hub slidably fitted within said housing, a needle extending from said needle hub extendable through said first opening, said needle hub passable through said second opening;
a spring element inside said housing for applying a biasing force against said needle hub towards said second end;
a key mechanism movably fitted to said passage of said housing, said key mechanism being movable to at least a first placement location and a second placement location relative to said housing, said key mechanism having a non-uniform opening configured to block the biased movement of said needle hub when said key mechanism is at said first placement location and to allow the retraction of the needle into said housing when said key mechanism is at said second placement location, the movement of said key mechanism being substantially orthogonal to the longitudinal axis of said housing; and
a plug coacting with said key mechanism, said plug movable from a first position to a second position relative to said key mechanism, said key mechanism being prevented from moving to said first placement location when said plug is at said first position and is movable to said second placement location when said plug is at said second position.

19. The butterfly needle assembly of claim 18, further comprising:
an elastic stopper at said second end of said housing for coacting against a collar of said needle hub to prevent said needle hub from completely passing out of said second opening when the needle is retracted into said housing.

20. The butterfly needle apparatus of claim 18, wherein said passage comprises a sleeve at the second end of said housing, and
wherein said key mechanism comprises a key slidable in said sleeve having at least two teeth each engageable with a catch at said sleeve so that said one portion of said non-uniform opening intersects the bore of said housing when said key is at said first placement location and a first of said teeth engages said catch, and wherein another portion of said non-uniform opening intersects the bore of said housing when said key is moved to said second placement location, a second of said teeth engaging said catch when said key is at said second placement location, the teeth being one way teeth to prevent said key from being moved from said second displacement location back to said first displacement location once said key has been moved form said first placement location to said second placement location.

21. A butterfly needle assembly, comprising:
a housing having a first end with a first opening and a second end with a second opening, a bore extending longitudinally along said housing, a passage orthogonal to the longitudinal axis of said housing in communication with the bore of said housing;
a needle hub slidably fitted within said housing, a needle extending from said needle hub extendable through said first opening, said needle hub passable through said second opening;
a spring element inside said housing for applying a biasing force against said needle hub towards said second end; and
a key mechanism movably fitted to said passage of said housing, said key mechanism being movable to at least a first placement location and a second placement location relative to said housing, said key mechanism having a non-uniform opening configured to block the biased movement of said needle hub when said key mechanism is at said first placement location and to allow the retraction of the needle into said housing when said key mechanism is at said second placement location, the movement of said key mechanism being substantially orthogonal to the longitudinal axis of said housing;
wherein said passage comprises a well upraised from said housing, and wherein said key mechanism comprises a button fitted to said well, said button comprising a base having two legs extending therefrom to form said non-uniform opening, a first portion of said non-uniform opening intersecting the bore of said housing when said button is at said first placement location and a second portion of said non-uniform opening intersecting the bore of said housing when said button is at said second placement location, the outside wall of each of said legs having a notch that engages with a catch from the inside wall of said well to maintain said first portion in place to abut a collar of said needle hub when said button is at said first placement location, a portion of said button being located above the mouth of said well at said first placement location.

22. The butterfly needle apparatus of claim 21, wherein said button is pushed into said well so that the top of said button is substantially flush with the top of said well when said button is moved to said second placement location, and wherein said second portion of said non-uniform opening is positioned in alignment with the bore of said housing at second placement location to enable said needle to be retracted into said housing.

* * * * *